United States Patent
Peters et al.

[11] Patent Number: 6,129,695
[45] Date of Patent: Oct. 10, 2000

[54] ATHLETIC BRACE

[76] Inventors: Rick Peters, 23 Hawthorne Hill, Louisville, Ky. 40204; Dolph Smith, 9133 Bluestone Cir., Indianapolis, Ind. 46236; Adam Smith, 10781 Woodmont La., Fishers, Ind. 46038

[21] Appl. No.: 09/175,485

[22] Filed: Oct. 20, 1998

Related U.S. Application Data

[63] Continuation-in-part of application No. 08/768,273, Dec. 18, 1996, abandoned.

[51] Int. Cl.[7] .................................................. A61F 13/00
[52] U.S. Cl. ................................. 602/62; 602/61; 602/63
[58] Field of Search ................................. 602/20, 21, 23, 602/26, 27, 60, 61, 62, 63, 64, 65, 66, 79; 607/96, 108, 109, 110, 111, 112

[56] References Cited

U.S. PATENT DOCUMENTS

| | | | |
|---|---|---|---|
| 5,395,399 | 3/1995 | Rosenwald | 607/111 X |
| 5,496,358 | 3/1996 | Rosenwald | 607/111 X |
| 5,624,386 | 4/1997 | Tailor et al. | 602/26 X |
| 5,643,185 | 7/1997 | Watson et al. | 602/26 |
| 5,792,084 | 8/1998 | Wilson et al. | 602/26 X |

*Primary Examiner*—Kim M. Lee
*Attorney, Agent, or Firm*—Theresa Fritz Camoriano; Camoriano and Associates

[57] ABSTRACT

The present invention provides an athletic brace in which the brace and a protective attachment are secured together as a single, unitary piece without stitching or glue. The protective attachment can have an intricate shape to fit around a moving body part, thereby permitting the therapeutic and protective use of braces that could not be achieved before. The protective attachment is anatomically secured in relation to a selected body part, and may provide control to an unstable joint, decrease stress to an over-worked tendon, provide pain relief to a sore muscle, and pad the area against impact that could cause further damage. An alternative embodiment of the present invention provides for a cushioned protective attachment on the brace to be protected by a protective shell brace.

58 Claims, 18 Drawing Sheets

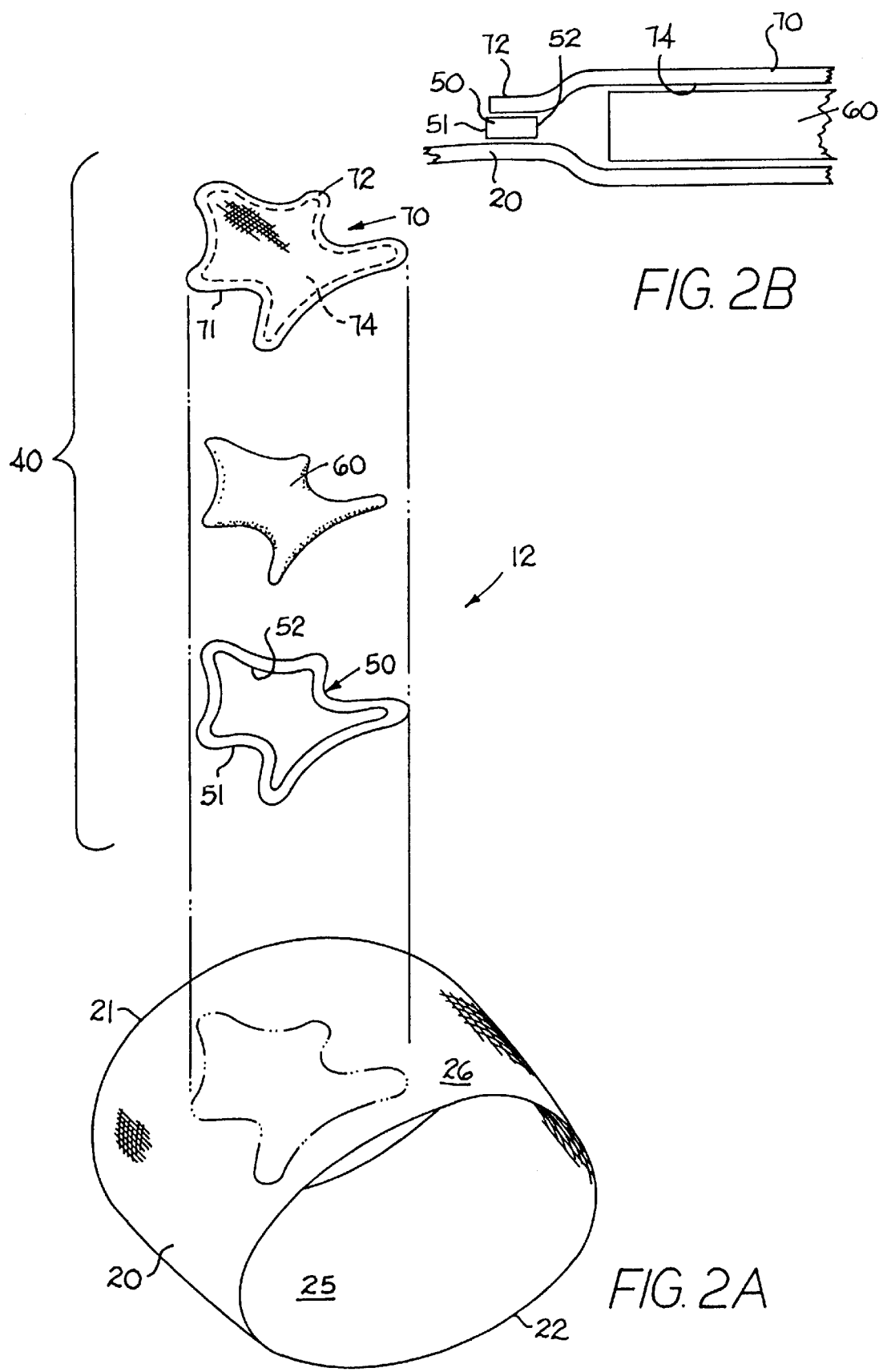

ATHLETIC BRACE

This is a continuation-in-part of application Ser. No. 08/768,273, filed Dec. 18, 1996 now abandoned.

BACKGROUND OF THE INVENTION

The present invention relates to athletic braces. It is known to provide athletic braces which are made of fabric that has been sewn into a tubular shape to slip over an arm or leg. However, the stitched seam often irritates the wearer, may come unraveled, and is labor-intensive to produce.

It is also known to provide athletic braces with protective attachments, such as cushions, foam pads or inflated bladders, which provide pressure against certain parts of the body for therapeutic purposes, for support, or for protecting certain parts of the body. However, in the past, it has been difficult to efficiently and effectively attach the protective cushioning to the braces. Typically, the protective attachments are either sewn or attached with glue onto the athletic brace, or a pocket may be sewn onto the brace, and the cushioning material inserted into the pocket.

Stitching requires substantial amounts of labor, and the resulting stitched seams on the brace can irritate the wearer. Also, stitching may come unraveled, resulting in failure of the seam. Glue can be difficult to precisely control, particularly when relatively narrow edges or intricate shapes are being joined, and the time required for the glue to set can result in increased production costs. Pockets do not secure the cushion as well as would be desired, because the cushion can shift relative to the pocket during use. Pockets also do not permit the use of intricately-shaped attachments.

Because of the constraints in the way the protective cushions have been attached to the brace, the cushions of the prior art have not been designed with intricate shapes to fit around a moving body part. Instead, protective cushions used on athletic braces generally have an oval or other simple shape. In many cases, this design feature does not provide optimum protection to the user.

Another form of protective attachment which has been used in conjunction with an athletic brace is the rigid brace. Rigid braces have been strapped onto the wearer's body along with the athletic brace to provide additional support and to provide protection against impact to the user. The straps typically are not as comfortable as an elastic brace. Rigid braces of the prior art have not been attached directly to the athletic brace, so they tend to shift during use. In addition, the rigid braces of the prior art have had very limited flexibility, making it difficult for them to conform to the knee, elbow, or other body part that bends and flexes on many different planes.

SUMMARY OF THE INVENTION

The present invention provides an athletic brace in which a protective attachment, having a thermoplastic adhesive layer, is secured to a brace having interstices. A bond is created between the protective attachment and the brace by melting the thermoplastic adhesive while applying pressure to the bonding area, and then cooling the bonding area while continuing to apply pressure. A preferred method for melting the adhesive uses high frequency energy, such as radio frequency voltage. The melting and cooling of the adhesive allows the adhesive to penetrate the interstitial areas on the brace, thereby fixing the protective attachment relative to the brace. The resulting bond has no stitched seams that can irritate the wearer or come unraveled during use.

The present invention provides an athletic brace in which the protective attachment can have an intricate shape to fit around a moving body part, thereby permitting the therapeutic and protective use of braces that could not be achieved before. Two features of the present invention allow for the intricate shape. First, the adhesive used to secure the protective attachment to the brace is a solid at ambient temperature, allowing the adhesive to be cut into the desired shape and allowing the adhesive placement on the brace to be precisely controlled. Second, the adhesive is preferably melted using high frequency voltage supplied through a die or electrode, which can be cut to the desired seam shape. Using a die to melt the adhesive to secure the protective attachment to the brace allows intricately shaped seams to be easily mass produced with consistent quality, a goal that is difficult to achieve with sewn seams.

The present invention further provides an athletic brace in which the protective attachment may be a rigid attachment. The rigid attachment can provide the user with a support that provides maximum stability to a body part. The present invention provides for scoring the rigid attachment to allow the attachment to flex in one direction, but which prevents the attachment from flexing in other directions, thereby further protecting the user.

BRIEF DESCRIPTION OF THE DRAWINGS

FIG. 2A is an exploded perspective view of the knee brace of FIG. 2;

FIG. 2B is a sectional view taken along the line 2B—2B of FIG. 2;

DESCRIPTION OF THE PREFERRED EMBODIMENTS

Figure 1:
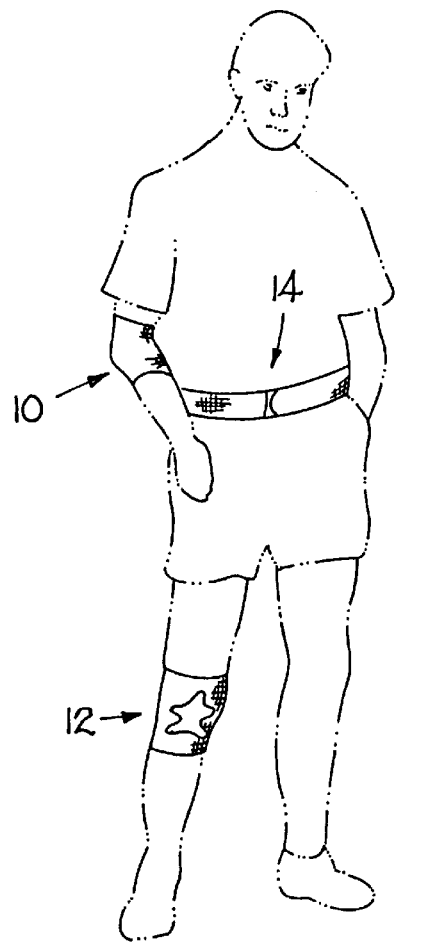
FIG. 1 is a drawing showing a person wearing three different types of braces made in accordance with the present invention.

FIG. 1 shows a person wearing an elbow brace 10, a knee brace 12, and a back brace 14. These are examples of some of the kinds of braces that may be made in accordance with the present invention. For illustrative purposes only, most of the embodiments described hereafter will refer to a knee brace. It is to be understood that the arrangements described in these embodiments could also be used in an elbow brace 10, a back brace 14, and in athletic braces for other body parts.

Figure 2:
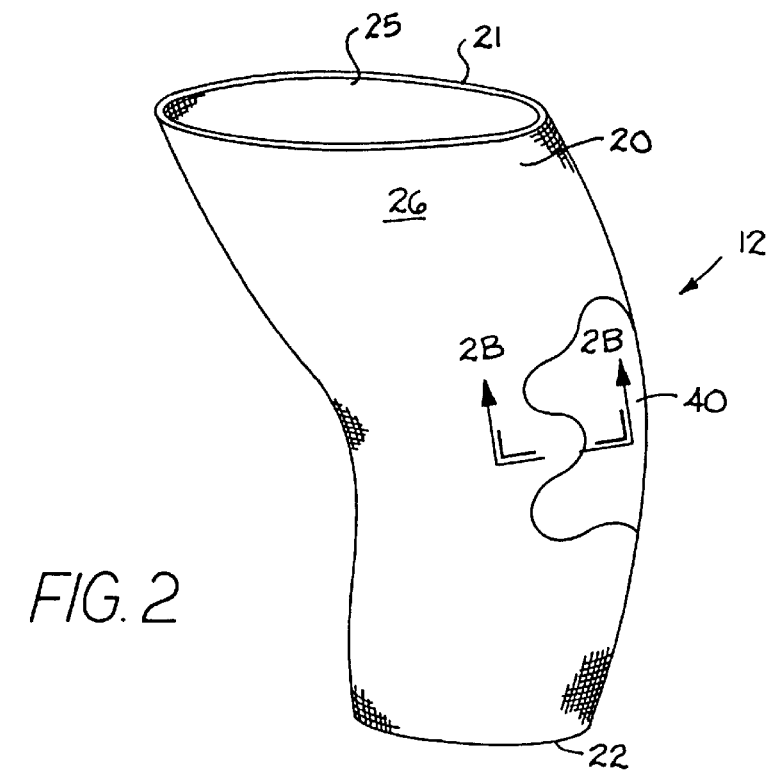
FIG. 2 is a perspective view of the knee brace of FIG. 1.

FIGS. 2, 2A, and 2B show the knee brace 12 in more detail. The knee brace 12 is made from a tubular sleeve or base 20 of flexible material which has a top edge 21, a bottom edge 22, an interior surface 25, and an exterior surface 26. The sleeve 20 is a single-layered, fabric-like material, having interstices. The material can be of any type having interstices, including woven, non-woven, or knitted materials. Example materials include nylon fabric, polyester fabric, lycra, polyurethane, Spandex®, knitted cotton elastic fabric, and combinations thereof. It is preferred that the material 20 be elastic, so it can flex as the person moves, for example, a material having an elasticity of at least 25%. The seamless, tubular shape of sleeve 20 is most commonly formed by a circular knitting process.

The brace 12 has a protective attachment 40 which is secured onto the base sheet 20. The protective attachment 40 can be secured either onto the interior surface 25 of the base 20 (shown later in FIG. 11), or onto the exterior surface 26, as shown in FIGS. 2 and 2A. The attachment 40 is preferably shaped so as to apply pressure to support the knee or to help prevent injury to the knee. The shape shown in the drawings is just an example. It is understood that a wide range of shapes could be used, depending upon the purpose of the brace. The protective attachment 40 includes an adhesive layer 50, a cushioning material 60, and a material cover 70. The adhesive layer 50, having a periphery 51 and an inside perimeter 52, is a single layer of thermoplastic material, such as ethyl vinyl acetate (EVA) copolymer, polyurethane, polyvinyl chloride (PVC), or any material that has a relatively high dielectric dissipation factor or that has thermoplastic properties. (The dielectric dissipation factor is a function of a material's dielectric constant and the loss tangent. A relatively high dielectric dissipation factor is defined herein as being greater than 0.04. For more information on dielectric dissipation factors and specific materials, see U.S. Pat. No. 5,427,645, issued to Lovin, and U.S. Pat. No. 4,857,129, issued to Jensen et al., incorporated herein by reference.) The material cover 70 is a single-layered, fabric-like material, having interstices. The material can be of any type having interstices, including woven, non-woven, or knitted materials. Example materials include nylon fabric, polyester fabric, lycra, polyurethane, Spandex®, knitted cotton elastic fabric, and combinations thereof. The cover 70 has a periphery 71 and an allowance 72. The allowance 72 is the margin along which the seam is formed. When the cover 70 is secured to the base 20 through the allowance 72, a niche space 74 is formed between the cover 70 and the base 20. The cushioning material 60, which fits within the niche space 74, is a material which can provide a measure of protection to the user, such as a foam cushion or a fluid-filled envelope. Example cushioning materials include vinyl nitrile foam, viscoelastic polyvinyl chloride foam, low density polyethylene foam, semi-rigid impact resistant materials, rigid impact resistant materials, or a combination thereof, or a bladder made of an impermeable material filled with a fluid, such as gas, liquid, gel, foam, or a combination thereof.

The protective attachment 40 is assembled by positioning the adhesive layer 50 on the sleeve 20, then placing the cushioning material 60 inside the inside perimeter 52 of the adhesive layer 50, and then placing the cover 70 over the adhesive layer 50 and cushioning material 60, such that the allowance 72 overlaps the adhesive layer 50. A radio-frequency ("RF-sealed") seam is made through the allowance 72 joining the base 20, the adhesive layer 50, and the cover 70, and encasing the cushioning material 60 in the niche space 74. FIG. 2B is a sectional view of the protective attachment 40 after it has been secured to the sleeve 20. The thicknesses of the materials have been exaggerated for illustration purposes only.

Radio-Frequency Bonds

Seams referred to throughout this application as RF-sealed seams are made using thermoplastic materials which are responsive to, or which can be melted when exposed to, radio frequency (RF) energy or voltage. The material directly in contact with the thermoplastic material can be one of two types. Either, it must also be a thermoplastic material responsive to RF energy, so that both it and the thermoplastic material melt in the heating process and blend together to form a unitary material, or it must have interstices (pores or spaces), so the thermoplastic material can flow into the interstitial regions when it is melted to form a mechanical bond. To make the second type of bond, the thermoplastic material is melted and flows into interstitial regions of the adjacent materials. When the energy source is removed, the thermoplastic material cools and sets within the interstitial regions, thereby creating a mechanical bond between the thermoplastic material and adjacent materials. The thermoplastic materials are melted and set by placing the thermoplastic materials, and the materials with interstices to which the thermoplastic materials are to be bonded, between a lower platen and an electrode, mounted on an upper platen, pressing the materials between the electrode and lower platen without applying an energy field, applying high (radio) frequency voltage to the materials under pressure for a short period of time to heat and melt the thermoplastic materials, then cooling the materials under pressure, thereby setting the bond between the materials. The amount of time the electrode and the lower platen press against the material before the voltage is applied is referred to as the "pre-seal time"; the amount of time the voltage is applied is the "seal time"; and the cooling period is the "dwell time". In theory, because a high frequency voltage is applied for a short period of time, the metal electrode and the lower platen remain relatively cool, i.e. remaining at ambient temperature while the thermoplastic materials are heated, and thus, the electrode and the lower platen can expedite the material cooling step by drawing heat away from the bonding region. However, because the electrode and the lower platen draw heat from the bonding region, during continuous production, the temperatures of the electrode and the lower platen increase over time from ambient temperature to an equilibrium temperature determined by the materials being bonded and the rate of production. To eliminate the need to modify the seal time and dwell time as the electrode and the lower platen temperatures increase, the electrode and the lower platen can be preheated to an optimum production temperature for the thermoplastic materials being sealed. This produces seals with consistent quality. For each embodiment presented herein, the electrode and the lower platen preheat temperatures are essentially equivalent and are referred to as "heated platen" temperatures.

Figure 15:
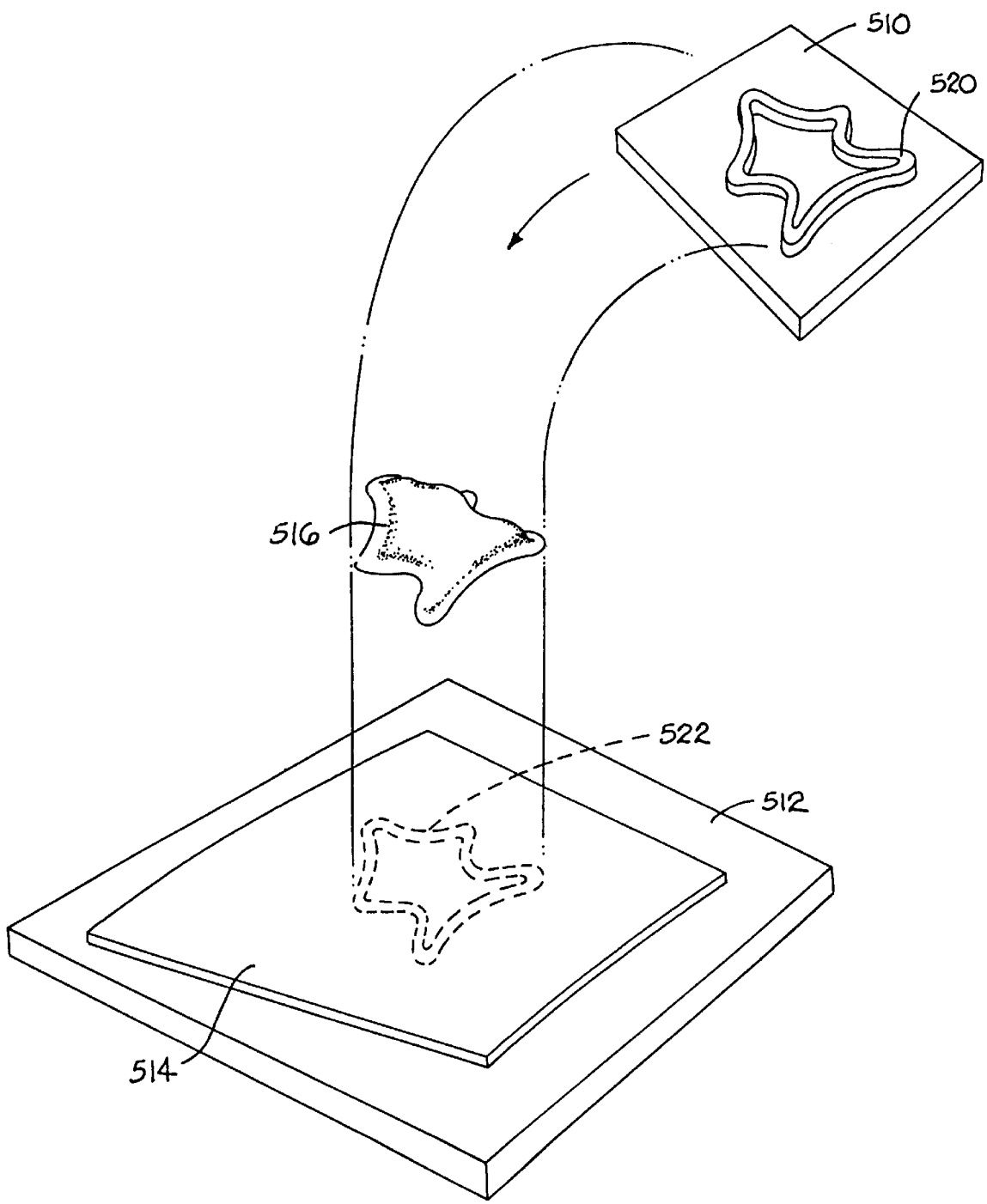
FIG. 15 is a schematic view of a electrode and platen with materials for RF bonding.

The radio frequency (RF) source used for the examples in this application is an eight kilowatt system manufactured by Thermex-Thermatron, Inc., 60 Spence Street, Bay Shore, N.Y., 11706, and sold under the product name Thermatron KF82. The Thermatron KF82 has an operating frequency of 27.12 MHz and uses a metallic electrode and a metal lower platen. FIG. 15 is a schematic view of an electrode 520, mounted to an upper platen 510, and a lower platen 512, further showing a thermoplastic material 516 and a second material 514, to be bonded together. The shape of the electrode 520 dictates the shape of the finished seam 522. As with metal dies, the electrode 520 can be cut with either a simple or an intricate design, as desired by the user. The lower platen 512 can be relatively flat, as shown, or it, too, can include a die defining recesses as desired, provided a flat region is provided to complement the electrode shape 520. Still referring to FIG. 15, the number of materials layered between the electrode 520 and the lower platen 512 can vary. At least one material, for example the layer 516, must be a thermoplastic material responsive to RF energy.

It is anticipated that the RF source conditions can be modified as necessary to accommodate changes in materials. It is further anticipated that other energy sources may be used to make the seams provided the energy source is capable of heating and melting the thermoplastic materials within a seal region without damaging materials in or surrounding the seal region.

EXAMPLE 1

Referring again to FIGS. 2, 2A, and 2B, in a preferred embodiment, the sleeve 20 is made of knitted cotton elastic material; the adhesive layer 50 is polyurethane, having a thickness of from about 0.006" to about 0.012"; the cushioning material 60 is vinyl nitrile foam, having a thickness of from about 0.125" to about 0.5"; and the cover 70 is made of knitted cotton elastic material, with an allowance 72 of from about 0.06" to about 1.0". In the most preferred embodiment, the sleeve 20 is made of knitted cotton elastic material; the adhesive layer 50 is polyurethane, having a thickness of about 0.008"; the cushioning material 60 is vinyl nitrile foam, having a thickness of about 0.5"; and the cover 70 is made of knitted cotton elastic material, with an allowance 72 of about 0.5". In the most preferred embodiment, the RF-sealed seam is made through the allowance 72 joining the sleeve 20, the adhesive layer 50, and the cover 70, and encasing the cushioning material 60, using a power setting of about 45%, pre-seal time of about 3 seconds, seal time of about 2.5 seconds, dwell time of about 4 seconds, pressure of about 70 PSI, and the heated platen at about 130° F.

Figure 3:
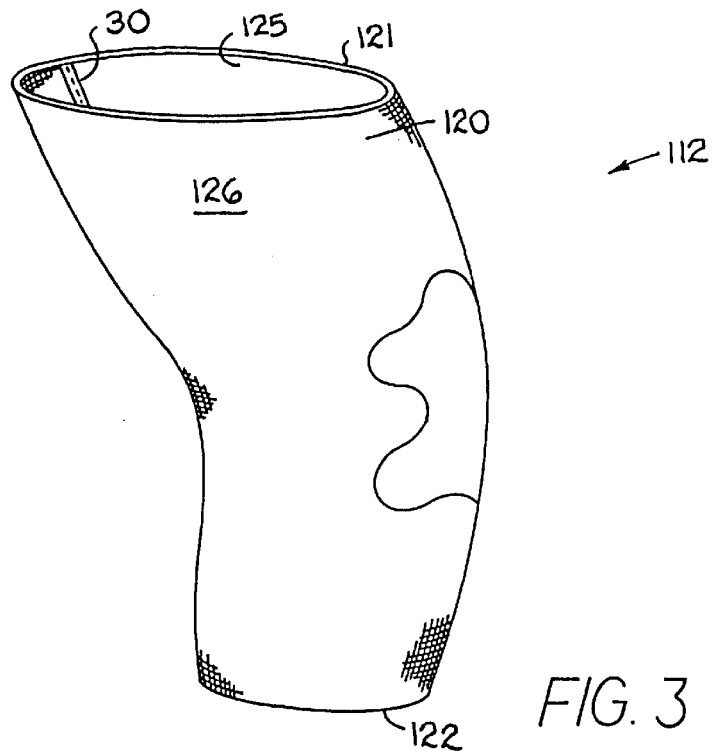
FIG. 3 is a perspective view of an alternative embodiment of the knee brace of FIG. 1.
Figure 3A:
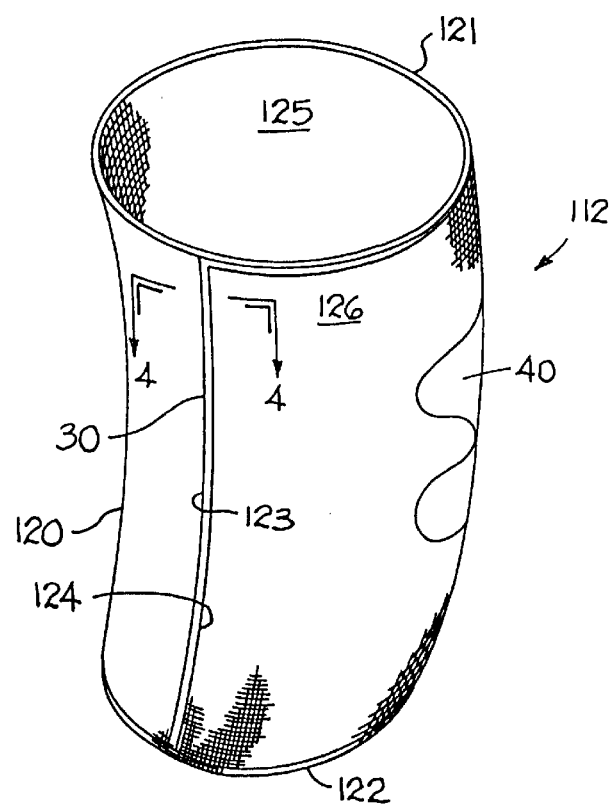
FIG. 3A is a rear perspective view of the knee brace of FIG. 3.
Figure 3B:
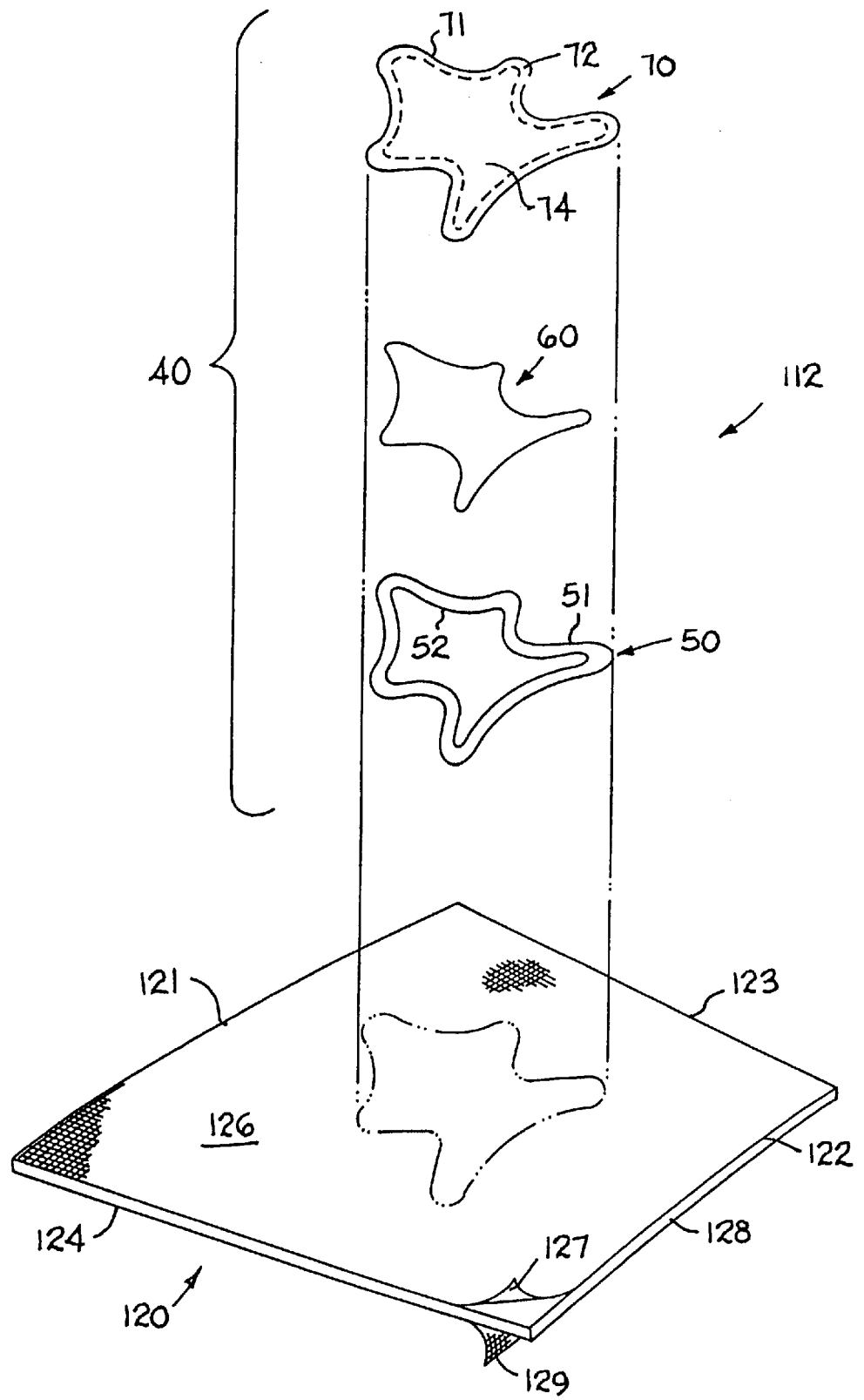
FIG. 3B is an exploded perspective view of the knee brace of FIG. 3 before the rear seam is made.

An alternative embodiment to the brace 12 is shown in FIGS. 3, 3A, and 3B as a seamed brace 112. The seamed brace 112 differs from the brace 12 in two respects—it uses a three-layered base material 120, and it includes a seam 30. The base 120, is a sheet, having a top edge 121, a bottom edge 122, a right edge 123, a left edge 124, an interior surface 125, and an exterior surface 126. It would be possible to make the base 120 from a single layer of material, as in the first embodiment. However, in this embodiment, the base 120 is a three-layered sandwiched material, having inner and outer flexible sheets 127, 129 laminated to an intermediate foamed polymer sheet 128, forming a material/foam/material structure. The flexible sheets 127, 129, are single layer, fabric-like materials, having interstices, similar to the single layer material 20 of FIG. 2. Example materials include nylon fabric, polyester fabric, lycra, polyurethane, Spandex®, knitted cotton elastic fabric, and combinations thereof. The inner flexible sheet 127 may be the same as or can be different than the outer flexible sheet 129. The foamed polymer 128 is preferably neoprene but can be other foamed olefin-based polymers, such as foamed polyethylene or foamed polypropylene. A commercially available example of a sandwiched three-layered base 120 is a nylon/neoprene/nylon material manufactured by Rubatex Corporation, 906 Adams Street, Bedford, Va. 24523, sold as a customized R-1400 product. The material sheets 127, 129 and foam 128 can be laminated together by any means which does not damage the components during the lamination process, such as mechanical lamination. Other lamination processes are known, including extrusion lamination, flame lamination, and adhesive lamination, and it is thought that any lamination method would work.

The sheet 120 is formed into a tubular shape by joining the right edge 123 and left edge 124 at the seam 30. The seam 30 may be made as a butt weld 32 or 32', shown in FIGS. 4 and 4A, or as a lap weld 34, shown in FIG. 5.

Figure 4:
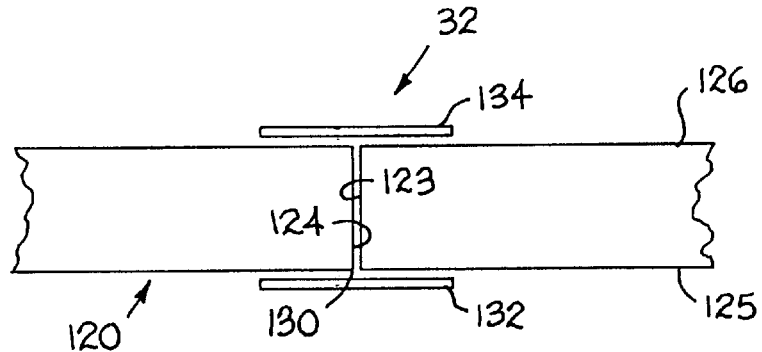
FIG. 4 is a view taken along the line 4—4 of FIG. 3A.

To form the butt weld 32 of FIG. 4, the right edge 123 and the left-edge 124 of the sheet 120 abut each other to form an abutting seam line 130. A first piece of a meltable elastomeric polymer 132, such as thermoplastic polyurethane, polyvinyl chloride (PVC), ethyl vinyl acetate (EVA), and combinations thereof, is positioned along the interior surface 125 covering the seam line 130. A second piece of meltable elastomeric polymer 134 is positioned along the exterior surface 126 also covering the seam line 130. The elastomeric polymers 132, 134 are then melted onto the sheet 120 using heat and pressure. The preferred method for applying heat and pressure is to use RF technology, as described earlier. In this case, since the weld 32 has no intricate shape, the electrode and lower platen used in the RF process can simply be flat.

Figure 4A:
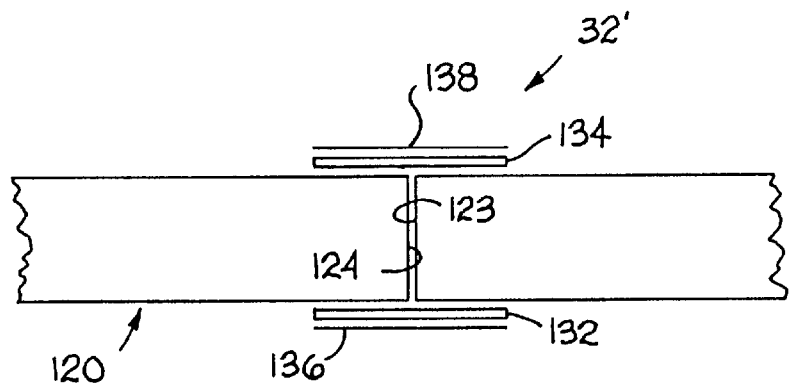
FIG. 4A is a view of a first alternative embodiment of the seam of FIG. 3.

When the butt weld 32 is formed as described above, the elastomeric polymers 132, 134 can be tacky and may irritate the wearer during use. As shown in FIG. 4A, a smoother surface can be made by covering the exposed surfaces of the polymers 132, 134, with first and second pieces of fabric 136, 138, respectively. The fabric pieces 136, 138 can be any fibrous material having interstices, such as nylon, lycra, polyester, cotton, knitted cotton elastic fabric, or a combination thereof. When pieces of fabric 136, 138, are used to cover the elastomeric polymers 132, 134, the polymers 132, 134 are melted to the sheet 120 and to the fabric pieces 136, 138, in a single operation producing a strong and elastic weld. The addition of the pieces of fabric 136, 138 can increase the strength and durability of the seam 32' because the melted elastomeric polymers 132, 134 can entwine the fabric fibers thereby making the fabrics 136, 138 a component of the resulting weld.

Figure 5:
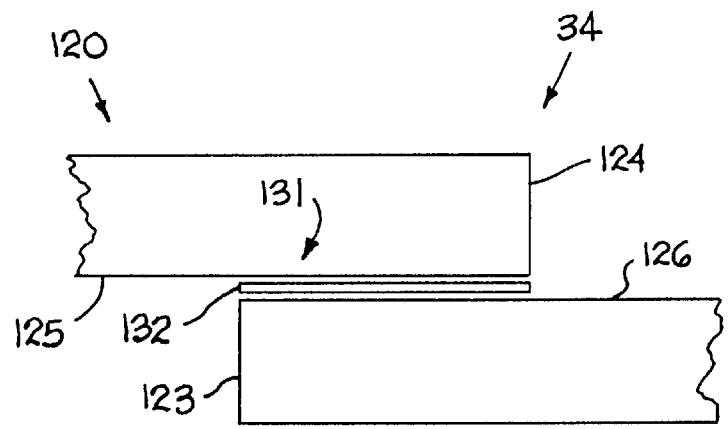
FIG. 5 is a view of a second alternative embodiment of the seam of FIG. 3.

The lap weld 34, shown in FIG. 5, can be made from the sheet 120 by overlapping the interior surface 125 of the left edge 124 and the exterior surface 126 of the right edge 123 to create an overlap seam line 131. A first piece of elastomeric polymer 132, having a length and a width substantially similar to the length and width of the overlap seam line 131, is placed between the interior surface 125 and the exterior surface 126, and an RF-sealed seam is made joining the left edge 124/polymer 132/right edge 123 layers.

The protective attachment 40 of the seamed brace 112 of FIGS. 3, 3A, and 3B, is identical to the attachment 40 of the previous brace 12. The attachment 40 can be secured either onto the interior surface 125 or onto the exterior surface 126 of the base 120, and it can be secured on the base 120 either before or after the base 120 is formed into the tubular shape by forming the seam 30.

EXAMPLE 2

Referring again to the seamed brace 112 in FIGS. 3, 3A, and 3B, in a preferred embodiment, the base 120 includes a foamed polymer layer 128 made of neoprene rubber, having a thickness of from about 0.060" to about 0.275", sandwiched between flexible sheets 127, 129 made of stretch nylon; the adhesive layer 50 is polyurethane, having a thickness of from about 0.006" to about 0.012"; the cushioning material 60 is vinyl nitrile foam, having a thickness of from about 0.125" to about 0.5"; and the cover 70 is made of stretch nylon, with an allowance 72 of from about 0.06" to about 1.0". An RF-sealed seam is made through the allowance 72 joining the sheet 120, the adhesive layer 50, and the cover 70, and encasing the cushioning material 60 in the niche space 74, using a power setting of about 40%, pre-seal time of about 2 seconds, seal time of about 2 seconds, dwell time of about 2 seconds, pressure of about 70 PSI, and the heated platen at about 130° F. A butt seam of the type shown in FIG. 4 is then made. The right and left edges 123, 124 are joined by abutting together the edges 123, 124, at the seam line 130, covering the seam line 130 along the interior surface 125 by a first piece of urethane 132, having a thickness of about 0.030", and covering the seam line 130 along the exterior surface 126 by a second piece of urethane 134, having a thickness of about 0.030", then bonding the neoprene and urethane pieces using with the Thermatron KF82 with a power setting of about 24%, pre-seal time of about 2 seconds, seal time of about 3 seconds, dwell time of about 4 seconds, pressure of about 80 PSI, and heated platen at about 200° F.

EXAMPLE 3

The brace 112 is made as in Example 2, except a lap seam of the type shown in FIG. 5 is used. The right and left edges 123, 124 are joined by overlapping the left edge interior surface 125 and the right edge exterior surface 126, placing a piece of urethane 132, having a thickness of about 0.030", between the interior and exterior surface 125, 126, then bonding the neoprene and urethane pieces using the Thermatron KF82 with a power setting of about 24%, pre-seal time of about 2 seconds, seal time of about 3 seconds, dwell time of about 4 seconds, pressure of about 80 PSI, and heated platen at about 200° F.

Figure 6:
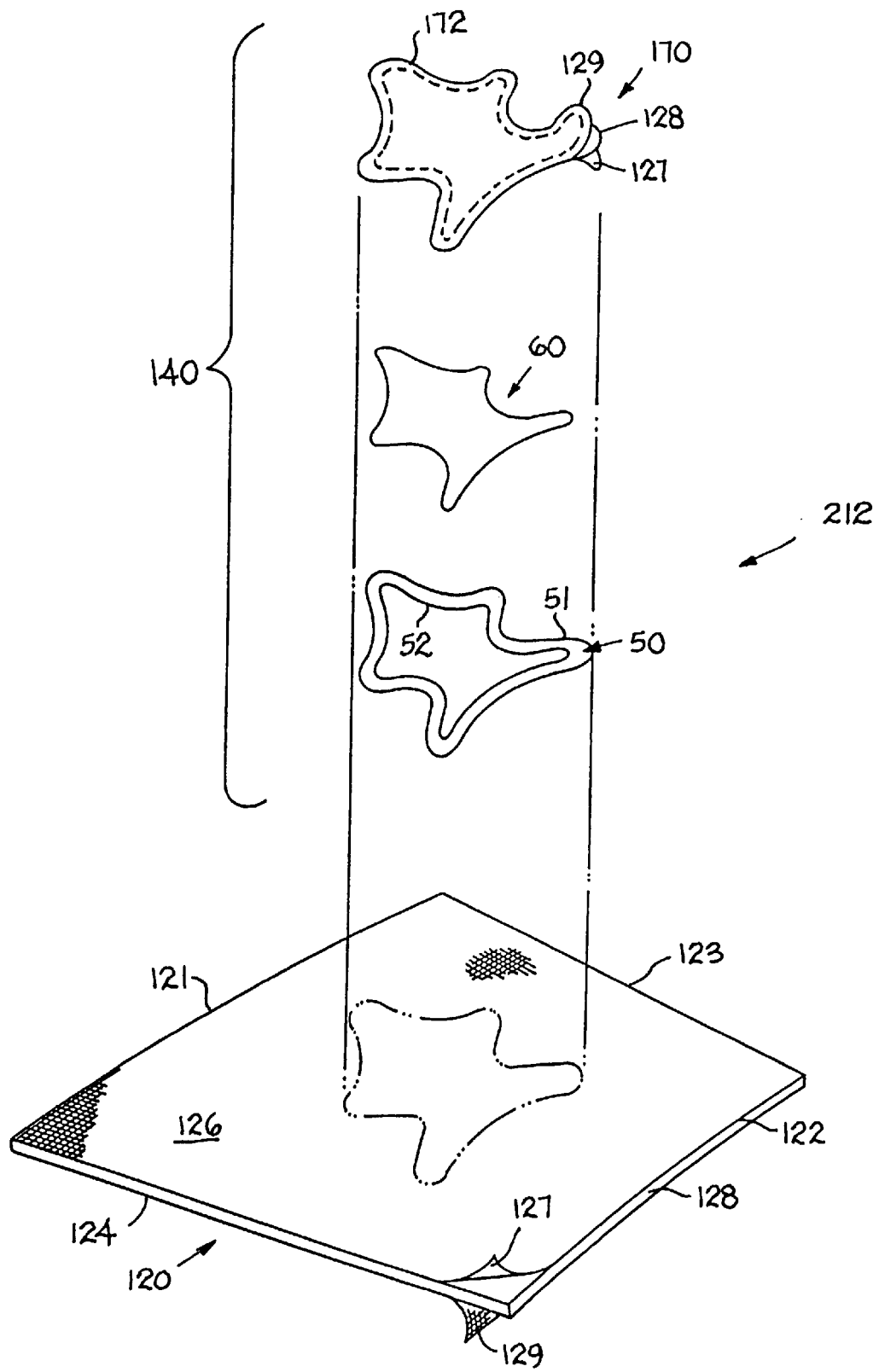
FIG. 6 is the same view as FIG. 3B, but showing a first alternative embodiment of the protective attachment.

The brace 212 of FIG. 6 is the same as the brace 112 of FIG. 3B, except that the cover 170 is made from a three-layered sandwiched material (material/foam/material), having layers 127, 128, 129, similar to the base 120. The cover 170 defines an allowance 172, where the seam is made.

EXAMPLE 4

In a preferred embodiment of the brace 212 in FIG. 6, the base 120 includes a foamed polymer layer 128 made of neoprene rubber, having a thickness of about 0.125", sandwiched between flexible sheets 127, 129 made of stretch nylon; the adhesive layer 50 is polyurethane, having a thickness of about 0.008"; the cushioning material 60 is vinyl nitrile foam, having a thickness of about 0.5"; and the cover material 170 includes a foamed polymer layer 128 made of neoprene rubber, having a thickness of about 0.060", sandwiched between flexible sheets 127, 129 made of stretch nylon, and having an allowance 172 of about 0.5". In the preferred embodiment, the RF-sealed seam is made through the allowance 172 joining the base 120, the adhesive layer 50, and the cover 170, and encasing the cushioning material 60 using a power setting of about 24.5%, pre-seal time of about 2 seconds, seal time of about 2.5 seconds, dwell time of about 6 seconds, pressure of about 80 PSI, and the heated platen at about 150° F. The right and left edges 123, 124 are then joined using a butt weld as described in Example 2.

Figure 7:
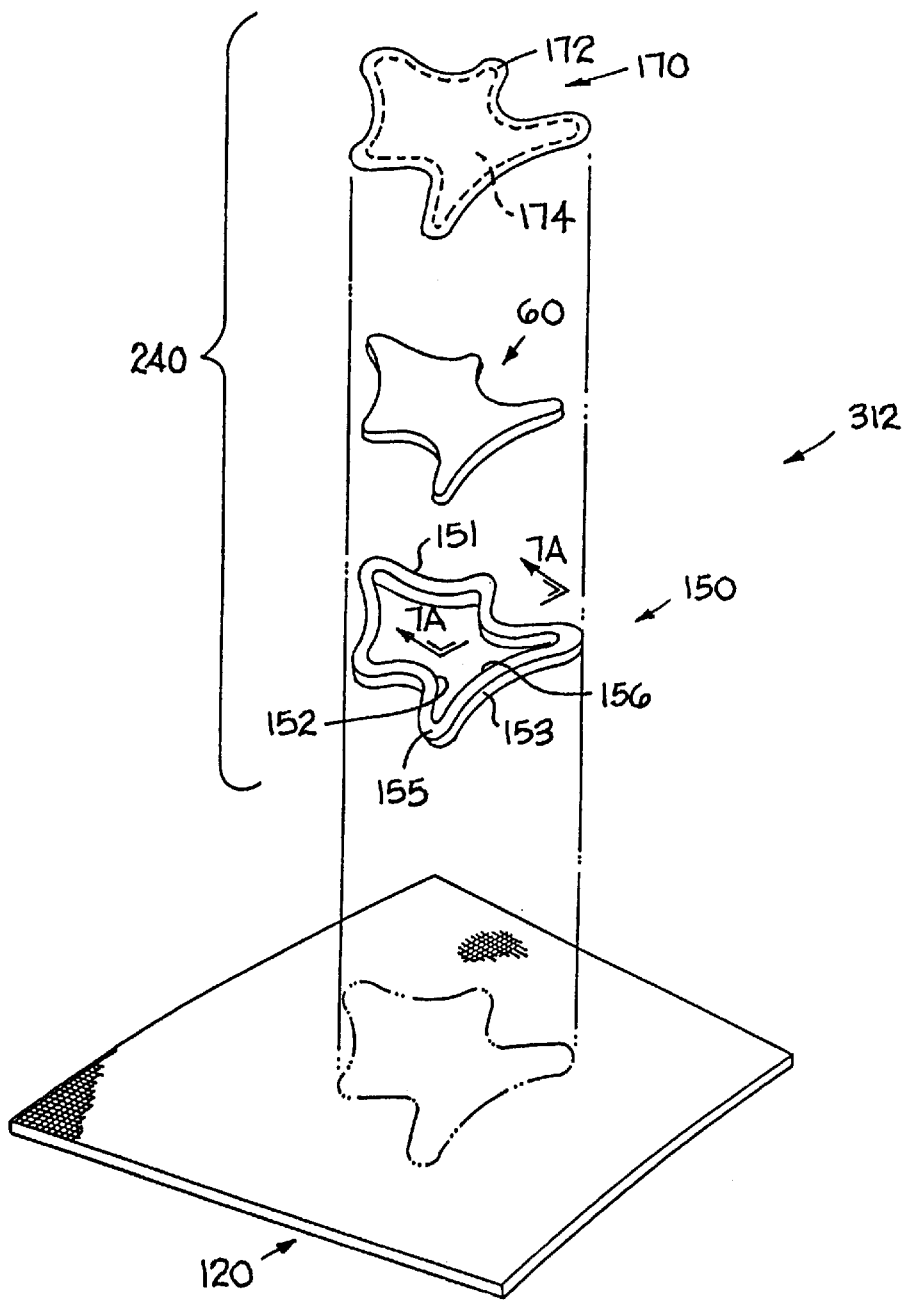
FIG. 7 is the same view as FIG. 3B, but showing a second alternative embodiment of the protective attachment.

FIG. 7 shows a brace 312 which is identical to the brace 212 of FIG. 6, except that, in this embodiment, the adhesive layer 150 of the protective attachment 240 is made of a thick, cushioned, adhesive composite material, having a periphery 151 and an inside perimeter 152. The adhesive composite 150, shown in greater detail in FIG. 7A, includes a meltable foam layer 153, such as low density polyethylene (LDPE) foam, laminated on both sides with thermoplastic film materials 154, 155. The adhesive/foam composite 150 is cut to the shape desired for the attachment 240, leaving a void space 156 defined by the inside perimeter 152. The cushioning material 60 is shaped to fit in the void space 156. The cover 170 is then fitted over the adhesive/foam composite 150 and the cushioning material 60, such that the periphery 151 of the adhesive/foam composite 150 is within the allowance 172 of the cover 170. An RF-sealed seam is made through the allowance 172, securing together the cover 170, the adhesive foam composite 150, and the base 120, and encasing the cushioning material 60 in a niche space 174, formed between the cover 170 and the base 120, similar to the niche space 74 of previous embodiments. An advantage of using the adhesive/foam composite 150 instead of the adhesive layer 50 of FIG. 6 is that the adhesive/foam composite 150 serves as a fixture to hold the cushioning material 60 during production.

EXAMPLE 5

In a preferred embodiment of the brace 312, the base 120, cushioning material 60, and cover 170, are the same as in Example 4. The adhesive/foam composite 150 has a meltable foam layer 153 made of LDPE, having a thickness of from about 0.125" to about 0.5", and thermoplastic film layers 154, 155 made of EVA copolymer, each having a thickness of from about 0.006" to about 0.012". In the most preferred embodiment, the base 120, cushioning material 60, and cover 170, are the same as in Example 4, and the adhesive/foam composite 150 has a foam layer 153, about 0.5" thick made of 1.6# LDPE, laminated on both sides with about 0.006" thick EVA copolymer layers 154, 155. In the most preferred embodiment, an RF-sealed seam is made across the allowance 172 joining the base 120, the adhesive composite 150, and the cover 170, and encasing the cushioning material 60. The RF-sealed seam is made using a power setting of about 29.5%, pre-seal time of about 3 seconds, seal time of about 12 seconds, dwell time of about 10 seconds, pressure of about 90 PSI, and the heated platen at about 235° F. The right and left edges 123, 124 are then joined using a butt weld as described in Example 2.

Figure 7A:
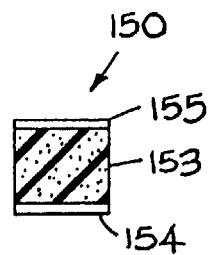
FIG. 7A is a view taken along line 7A—7A of FIG. 7.
Figure 7B:
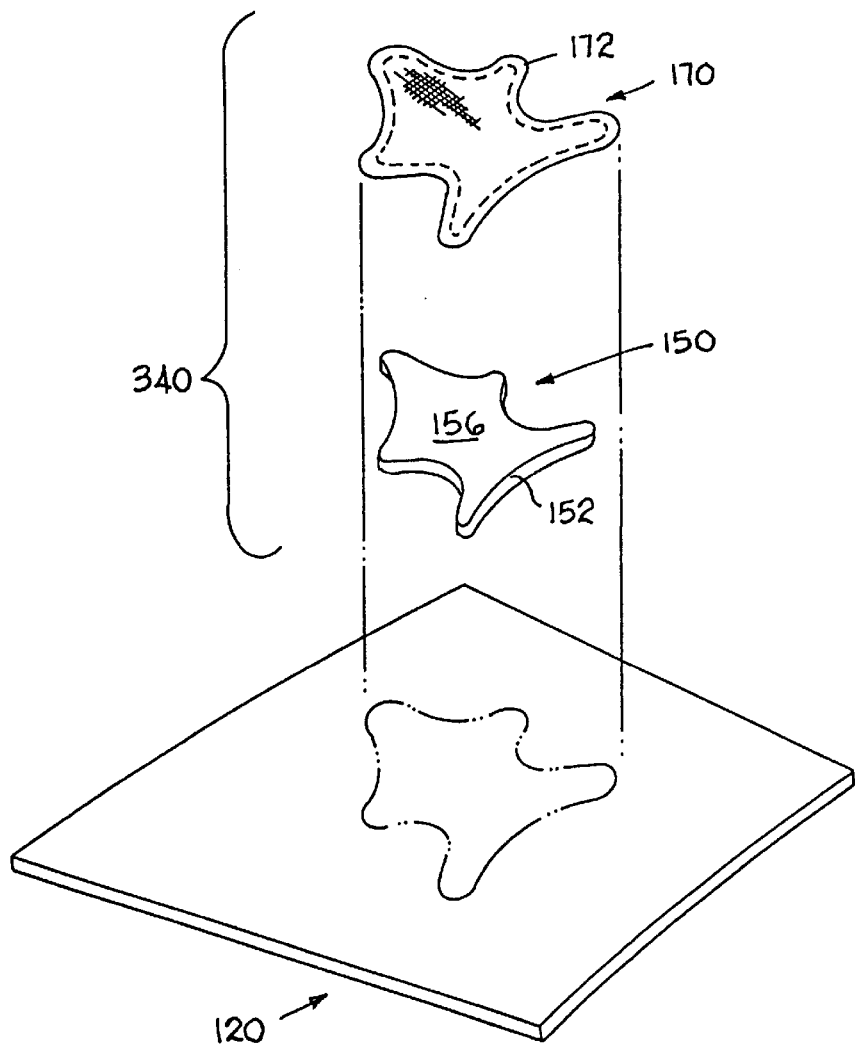
FIG. 7B is the same view as FIG. 3B, but showing a third alternative embodiment of the protective attachment.

FIG. 7B shows a brace 412, which is the same as the brace 312 of FIG. 7, except that the cushioning material 60 is eliminated, and the adhesive/foam composite 150' has no void space, so that the adhesive/foam composite 150' extends into the niche area and serves as the cushioning material for the protective attachment 340 without additional cushioning materials. An RF-sealed seam made through the allowance 172 joins the allowance portion 172 of the cover 170, the portion of the adhesive composite 150' that is within the allowance 172, and the portion of the base 120 that is within the allowance 172. The portion of the composite 150' which is not within the allowance 172 retains its cushioning properties.

EXAMPLE 6

The materials and RF-sealing conditions for the brace 412 are identical to Example 5, except that the vinyl nitrile foam cushion is not included in the protective attachment 340, and the adhesive composite 150' is cut to fill the area under the cover 170.

Figure 7D:
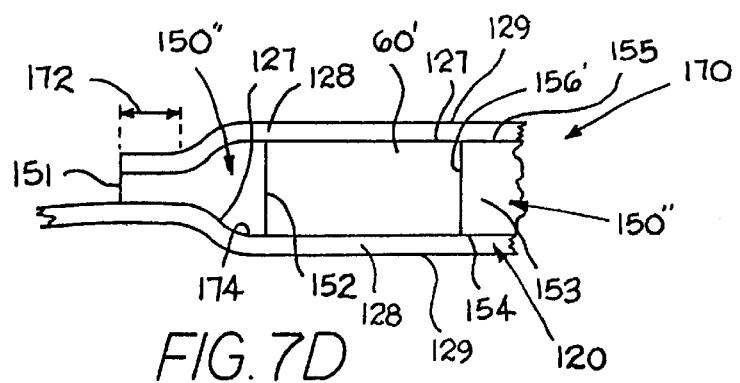
FIG. 7D is a sectional view taken through the attachment of the assembled embodiment of FIG. 7C.
Figure 7C:
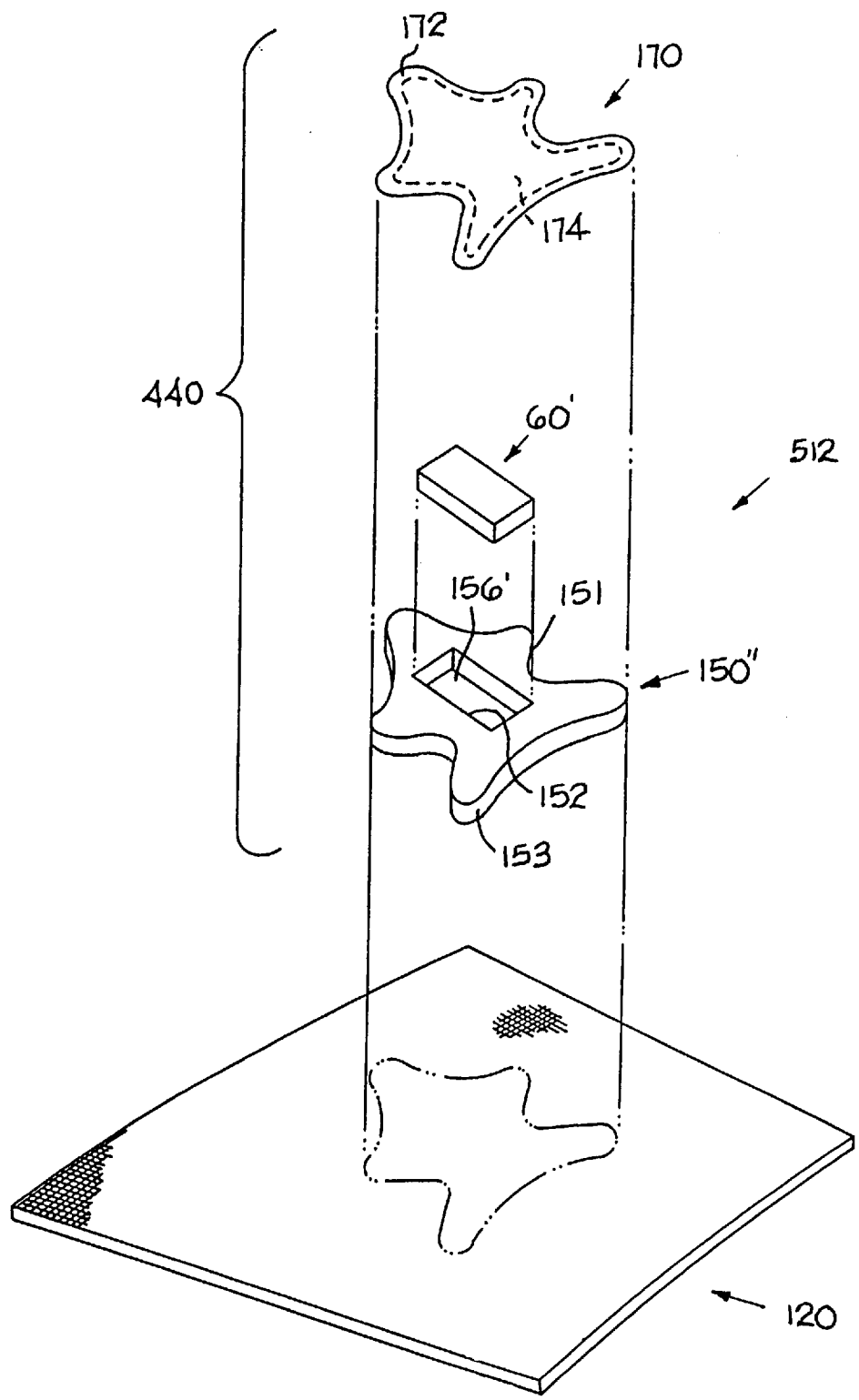
FIG. 7C is the same as FIG. 7, except the shapes of the adhesive/foam composite and the cushioning material have been modified.

FIGS. 7C and 7D show a brace 512, which is the same as the brace 312 of FIG. 7, except that the shape of the cushioning material 60' and the shape of the void space 156' of the adhesive/foam composite 150" have been changed. As with the previous embodiments, the cushioning material 60' is shaped to fit in the void space 156'. In this embodiment, the adhesive/foam composite 150" extends into the niche space 174, as in the embodiment of FIG. 7B. Because the adhesive/foam composite 150" includes a foam layer 153 (as shown in FIG. 7A), the composite 150" serves as a cushion in the area between the cushioning material 60' and the cover allowance 172, and the foam layer 153 can stabilize the positioning of the other cushioning materials 60' so they do not shift during use. Thus, this design permits different types of cushions in different parts of the niche space 174, which may be desirable in some applications—with the composite 150" providing cushioning around the edges and the cushioning material 60' providing a different type of cushioning in the center. Also, since the cushion 60' does not have to match the outer contour of the protective attachment, production costs are reduced. An RF-sealed seam adheres together the allowance portion 172 of the cover 170, the portion of the adhesive composite 150" that is within the allowance 172, and the portion of the base 120 within the allowance 172. The cushioning material 60' is encased between the cover 170 and the base 120, and is within the void space 156' of the composite 150", and that portion of the composite 150" which is not within the allowance 172 retains its cushioning properties. It would also be possible to make the cushioning material 60' of different layers, if desired.

Figure 8:
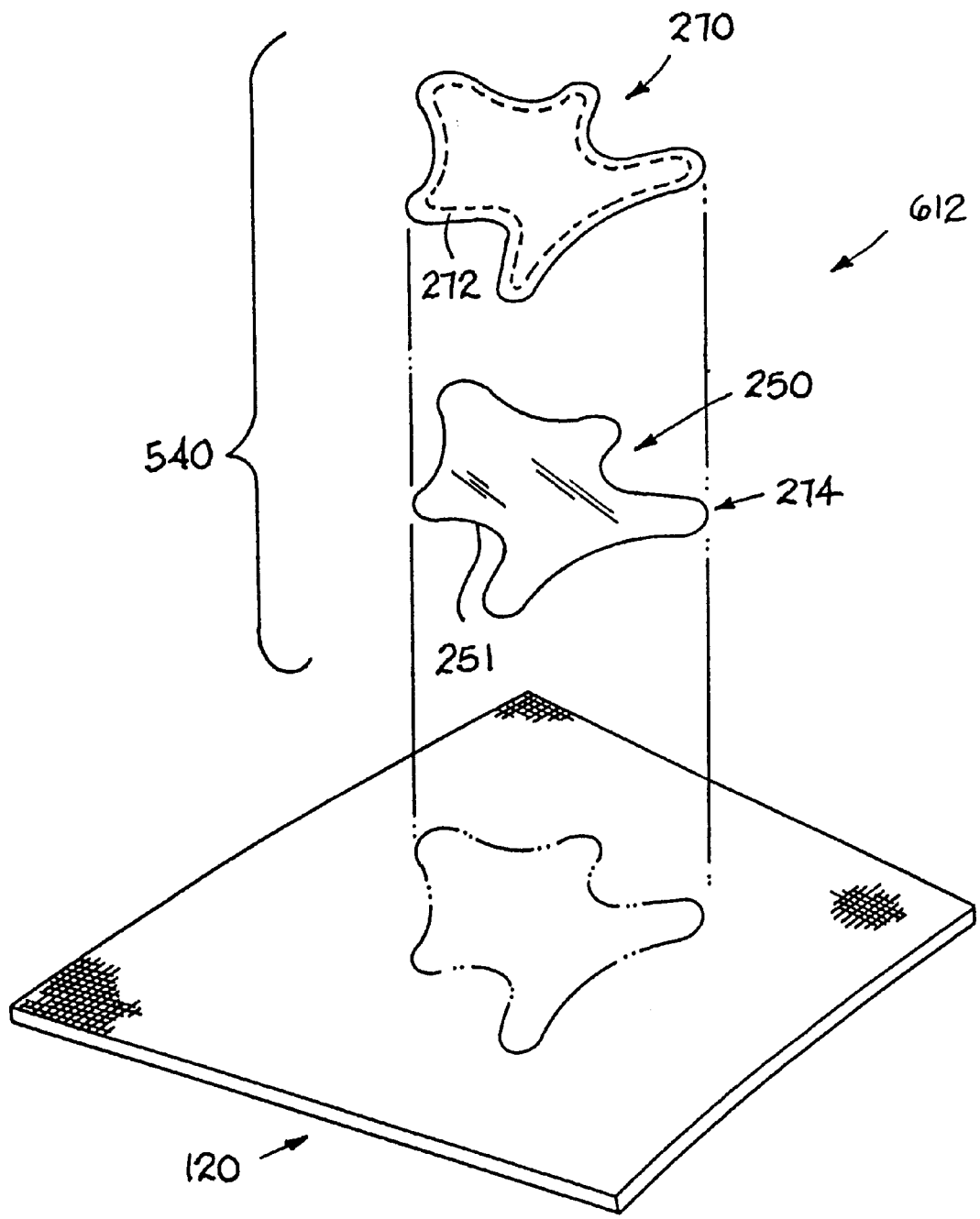
FIG. 8 is the same view as FIG. 3B, but showing a fourth alternative embodiment of the protective attachment.

FIG. 8 shows a brace 612, in which the protective attachment 540 is a bladder, made of an adhesive material layer 250, having a periphery 251, and a thermoplastic cover 270, having an allowance 272. The adhesive material 250 and the thermoplastic cover 270 are impermeable thermoplastic films having a high tensile strength, such as polyvinyl chloride (PVC) film, urethane film, or any material that is impermeable to fluid flow and that has thermoplastic properties when exposed to heat and pressure. The films 250, 270 are cut and may be vacuum formed, if desired. The bladder 540 is made by positioning the adhesive layer 250 on the base 120, covering the adhesive layer 250 with the thermoplastic cover 270, and making an RF-sealed seam, joining the allowance portion 272 of the thermoplastic material 270, the adhesive material 250, and the base 120, leaving an opening at a tail 274 through which a cushioning material can be added.

The cushioning material can be any fluid material which can provide a measure of protection to the user, such as gas, liquid, gel, or foam. The cushioning material is fed into the bladder 540 through the opening at the tail 274. After the bladder 540 is filled, the opening can be permanently sealed, for example, by making an RF-sealed seam. As an alternative, a valve can be provided on the bladder 540 through which the cushioning material can be added. If a valve is provided, it is not necessary to leave an opening when the RF-sealed seam is made.

Figure 8A:
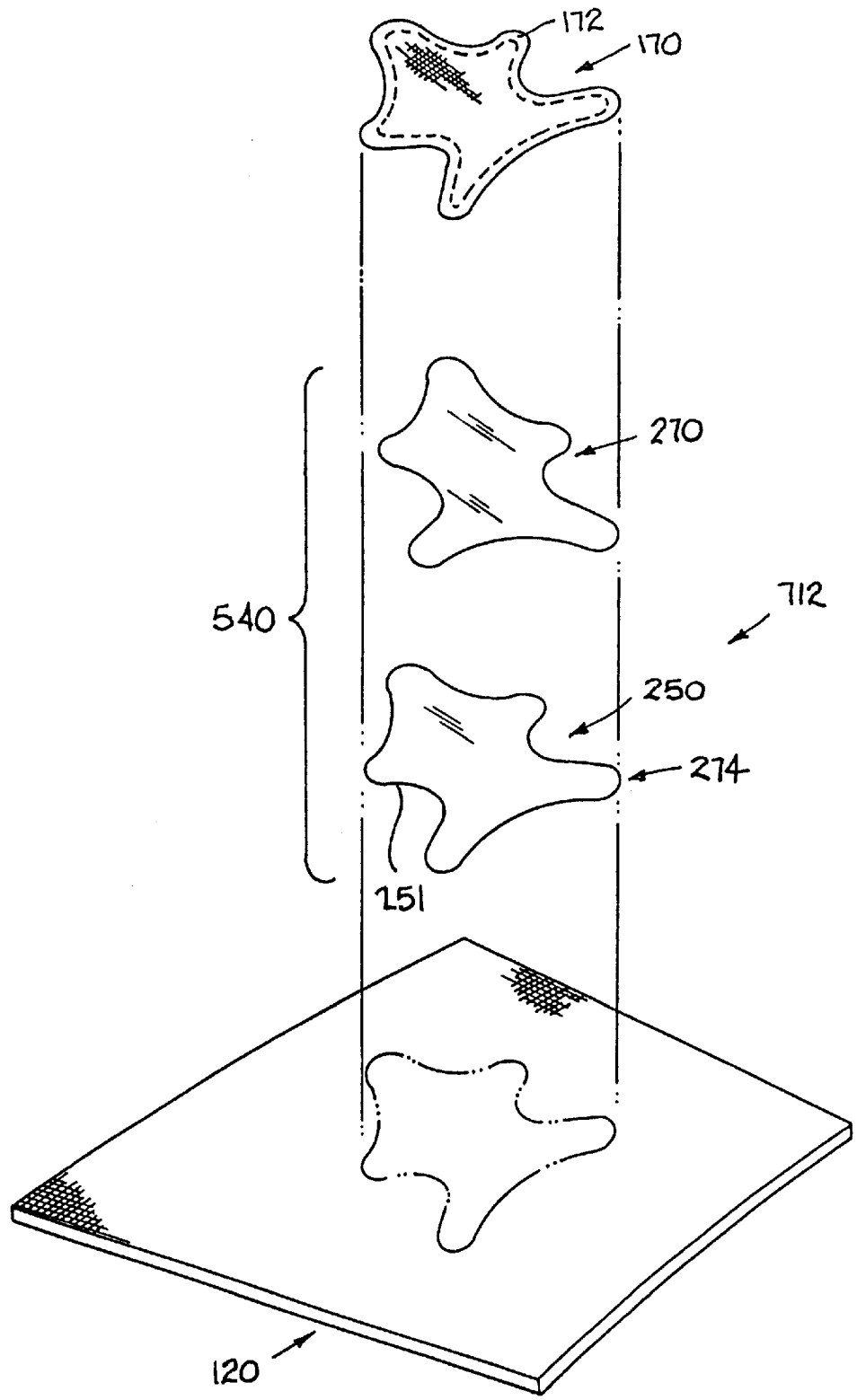
FIG. 8A is the same as FIG. 8, except that an additional material layer has been added to cover the bladder.

FIG. 8A shows a brace 712, which is the same as the brace 612 of FIG. 8, except that a material cover 170 has been added on top of the protective attachment 540. The cover 170, thermoplastic cover 270, adhesive layer 250, and base 120 are joined in a single step by making an RF-sealed seam across the cover allowance 172.

EXAMPLE 7

Referring to FIG. 8A, in the preferred embodiment, the base 120 and cover 170 are the same as in Example 4; the adhesive layer 250 and the thermoplastic cover 270 are PVC films, each having a thickness of about 0.012"; and the cushioning material is an aqueous gel. In the preferred embodiment, an RF-sealed seam is made through the allowance 172, joining the base 120, the adhesive layer 250, the thermoplastic cover 270, and the cover 170, but leaving a 0.5" wide opening at the tail 274, using a power setting of about 55%, pre-seal time of about 3.5 seconds, seal time of about 4.5 seconds, dwell time of about 5 seconds, pressure of about 80 PSI, and the heated platen at about 150° F. The cushioning material is fed in through the opening at the tail 274, then the opening is sealed using a power setting of about 40%, pre-seal time of about 2 seconds, seal time of about 2 seconds, dwell time of about 2 seconds, pressure of about 70 PSI, and the heated platen at about 130° F. The right and left edges 123, 124 are then joined using a butt weld as described in Example 2.

Figure 9:
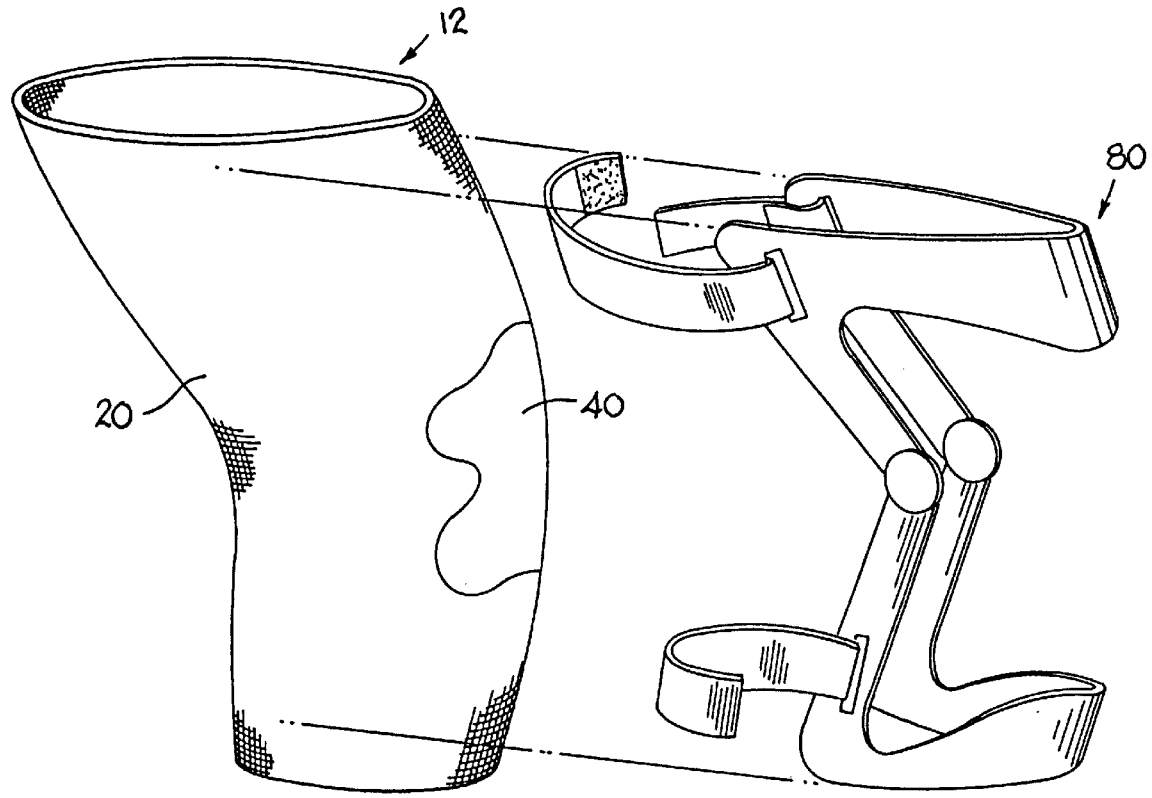
FIG. 9 is an exploded perspective view of the brace of FIG. 2 with a strap-on rigid brace added.
Figure 9A:
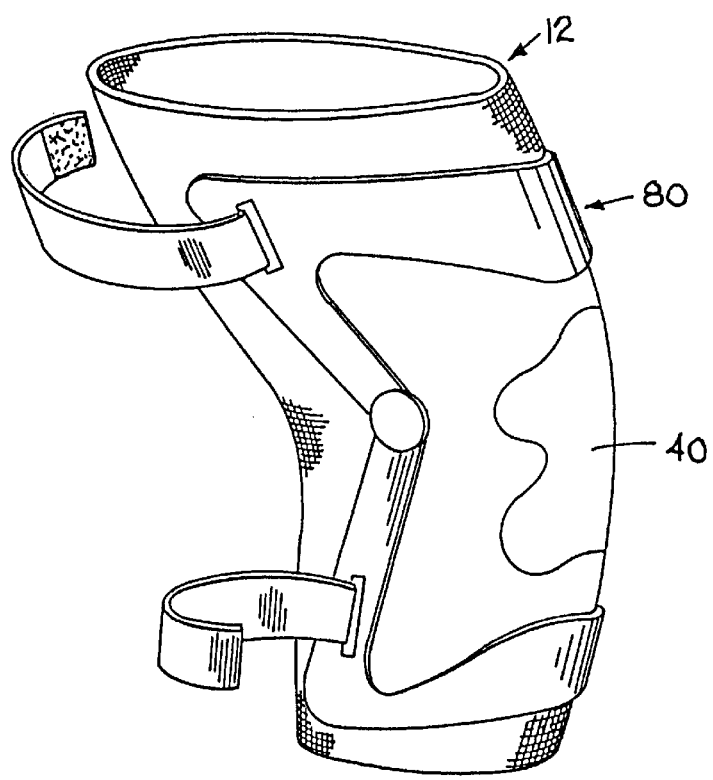
FIG. 9A is a perspective view of the combination of the rigid brace and the knee brace of FIG. 9.
Figure 9B:
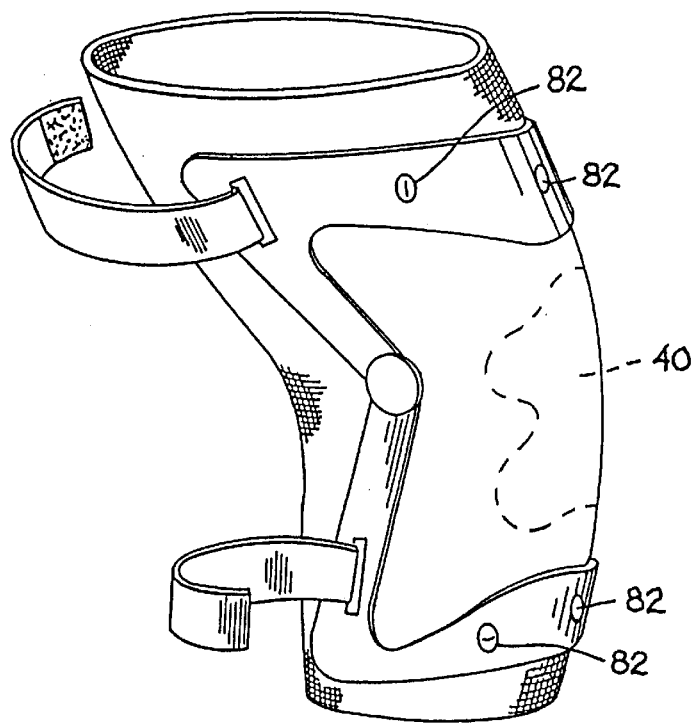
FIG. 9B is the same as FIG. 9A, except that the rigid brace is permanently secured to the knee brace.

Another form of protective attachment which can be used in conjunction with an athletic brace is a rigid brace. FIGS. 9 and 9A show a rigid brace 80 added on top of the knee brace 12 of FIG. 2, to provide additional support to the knee against impact. In FIGS. 9 and 9A, the rigid brace 80 is not attached directly to the athletic brace 12, so the rigid brace 80 can shift during use. FIG. 9B shows an example of a rigid brace 80 attached to the knee brace 12 at adhesion points 82. The rigid brace 80 can be adhered to the stretchable brace 12 by RF welding, by gluing, or by any known means of securing the braces.

Figure 10:
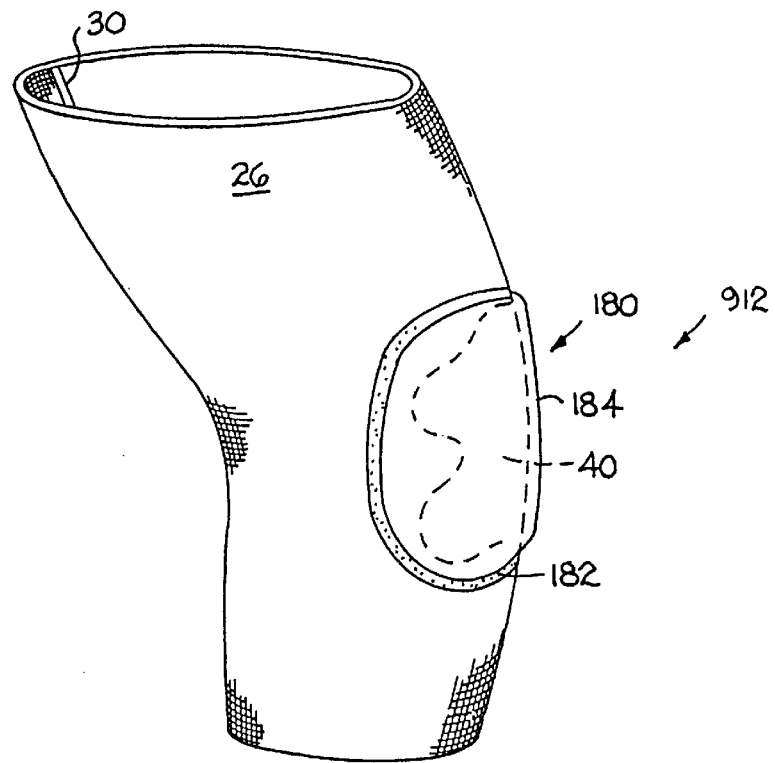
FIG. 10 is a perspective view of the brace of FIG. 3, turned inside-out, with a formed shell rigid protective attachment on the outside of the brace.
Figure 10A:
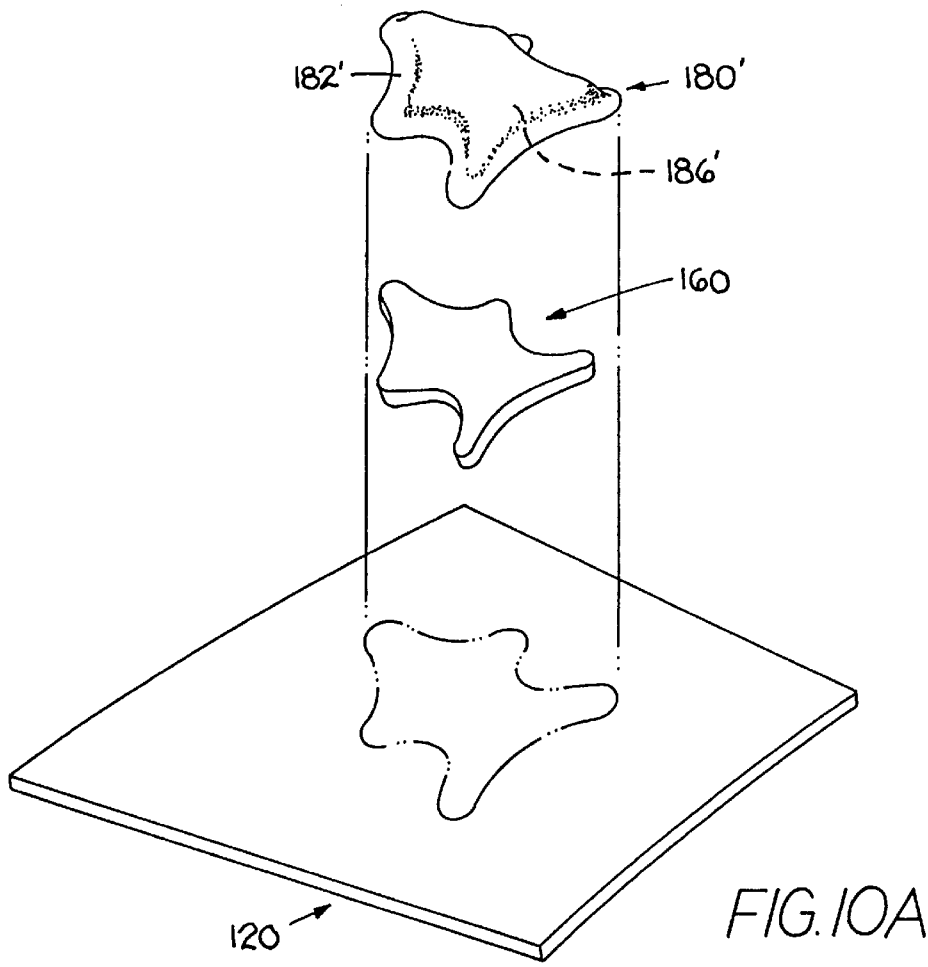
FIG. 10A is the same view as FIG. 3B, but showing a fifth alternative embodiment of the protective attachment.
Figure 10B:
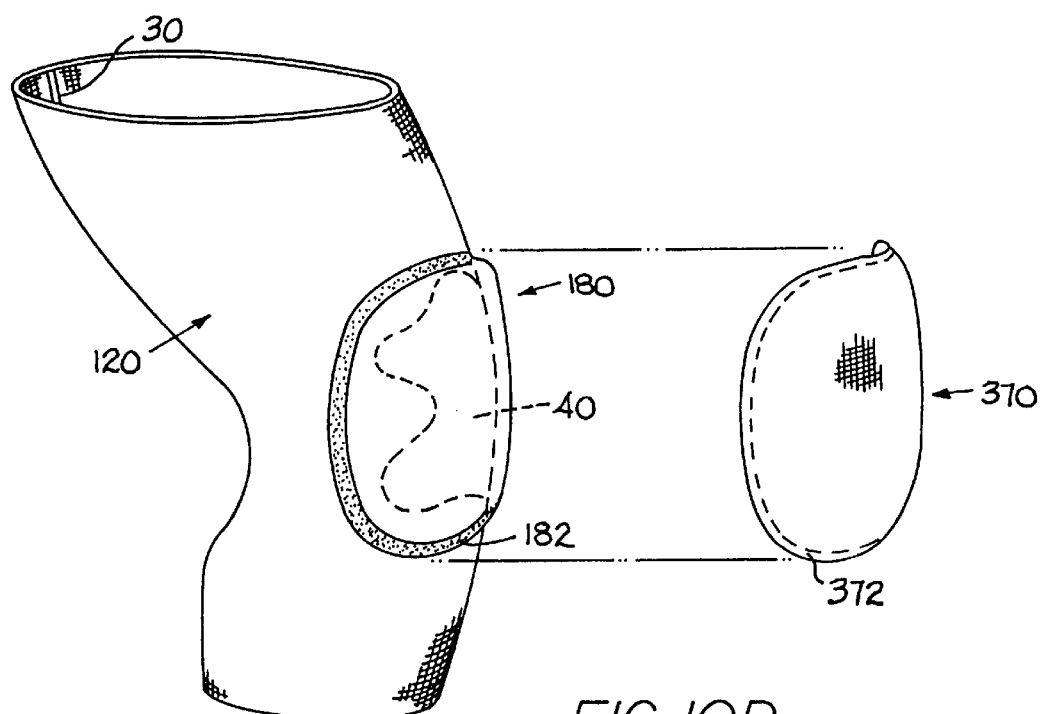
FIG. 10B is the same as FIG. 10, except that an additional cloth layer has been added to the outside of the rigid protective attachment.

FIGS. 10, 10A and 10B show braces including a formed shell 180 or 180'. The formed shell 180, 180' can protect the cushioning material of the athletic brace, in addition to protecting the user.

FIG. 10 shows a brace 912 including a formed shell 180, having an allowance 182 and a convex surface 184, attached to the knee brace 112 of FIG. 3. In this case, the brace 112 has been turned inside-out, so the protective attachment 40 is on its interior, and the formed shell 180 is attached to the exterior. The formed shell 180 similarly could be attached to the brace 12 of FIG. 2.

The formed shell 180 can be made of a rigid or semi-rigid meltable material, such as polyvinyl chloride (PVC), polyethylene terephthalate (PET), amorphous polyethylene terephthalate (APET), high density polyethylene/ethylvinyl acetate (HDPE/EVA) copolymer, glycol-modified polyethylene terephthalate (PETG), or any suitably rigid dielectrically responsive material, having a Rockwell Hardness R-value of at least 50 based on ASTM test method d-785. As shown in FIG. 10A, the meltable plastic shell 180' can be thermoformed into any shape, but the shape must include an allowance 182'. A niche space 186 is formed between the shell 180' and the base 120. The shell 180' may be formed with distinctive, equal-width side walls, or the shape may be irregular. An advantage of an irregularly shaped shell, that is, one having peaks and valleys, is that the contour of the formed shell may mirror the body's structure, thus providing the user with maximum stability, therapy, and padding for any particular body part. In addition, peaks and valleys may significantly reduce the migration of the overall support by adapting to and flexing with the shape of the body part.

Because the formed shell 180, 180' is made of a meltable plastic material, it can be directly attached to a material having interstices, such as the base 120, without the need for additional adhesive materials—the formed shell 180, 180' is positioned on the base 120, and an RF-sealed seam is made across the allowance 182, 182'. In a like manner, the shell 180, 180' can be attached to the sleeve 20 of FIG. 2.

FIG. 10A shows that the niche space 186 can hold a cushioning material 160, such as a piece of foam or a bladder, similar to the cushioning material of previous embodiments. The cushioning material 160 may fill less than the entire volume of the niche space 186. When a cushioning material 160 is added, the cushioning material 160 is positioned within the niche space 186 before the shell 180' is secured to the base 120. In FIG. 10A, the protective attachment 40 of FIG. 10 has been eliminated, so the protective attachment is the shell 180' and cushion 160.

The brace 912 of FIG. 10B is the same as the embodiment of FIG. 10, except that an external covering 370 has been added over the formed shell 180. The covering 370, having an allowance 372, can be essentially the same as the single-layered cover 70 or the three-layered material 170 of previous embodiments. The covering 370 and shell 180 are secured to the brace 112, in a single operation, by an RF-sealed seam made across the allowances 182, 372, thereby joining the covering 370, the formed shell 180, and the brace 112.

EXAMPLE 8

Referring to FIG. 10, the brace 112 of Example 4 is made and turned inside out, and the formed shell 180 is made of PVC, having a thickness of from about 0.020" to about 0.080", with an allowance 182 of from about 0.125" to about 0.5". In a most preferred embodiment, the brace 212 of Example 4 is made and turned inside out; the formed shell 180 is made of about 0.050" thick PVC, with an allowance 182 of about 0.375"; and an RF-sealed seam is made through the allowance 182 joining the base 120 and the formed shell 180, using a power setting of about 50%, pre-seal time of about 2.5 seconds, seal time of about 5 seconds, dwell time of about 6 seconds, pressure of about 80 PSI, and the heated platen at about 160° F.

EXAMPLE 9

Referring to FIG. 10B, the materials are the same as Example 8, except that a material cover 370, having a foamed polymer layer 128 made of neoprene rubber and having a thickness of from about 0.060", sandwiched between flexible sheets 127, 129 made of stretch nylon, and having an allowance 172 of about 0.5", is positioned over the formed shell 180. In the preferred embodiment, the RF-sealed seam is made through the allowance 372 joining the base 120, the formed shell 180, and the cover 370, using a power setting of about 55%, pre-seal time of about 3.5 seconds, seal time of about 4.5 seconds, dwell time of about 5 seconds, pressure of about 80 PSI, and the heated platen at about 150° F.

EXAMPLE 10

Referring to FIG. 10A, the base 120 is the same as in Example 4, the cushioning material 160 is a LDPE sheet, and the shell 180 is made of PVC, having a thickness of from about 0.020" to about 0.040", with an allowance 182 of from about 0.125" to about 0.5". The RF-sealed seam is made through the allowance 182, joining the base 120 and the shell 180, and encasing the cushioning material 160, using a power setting of about 45%, pre-seal time of about 3 seconds, seal time of about 2.5 seconds, dwell time of about 4 seconds, pressure of about 70 PSI, and the heated platen at about 130° F.

Figure 11:
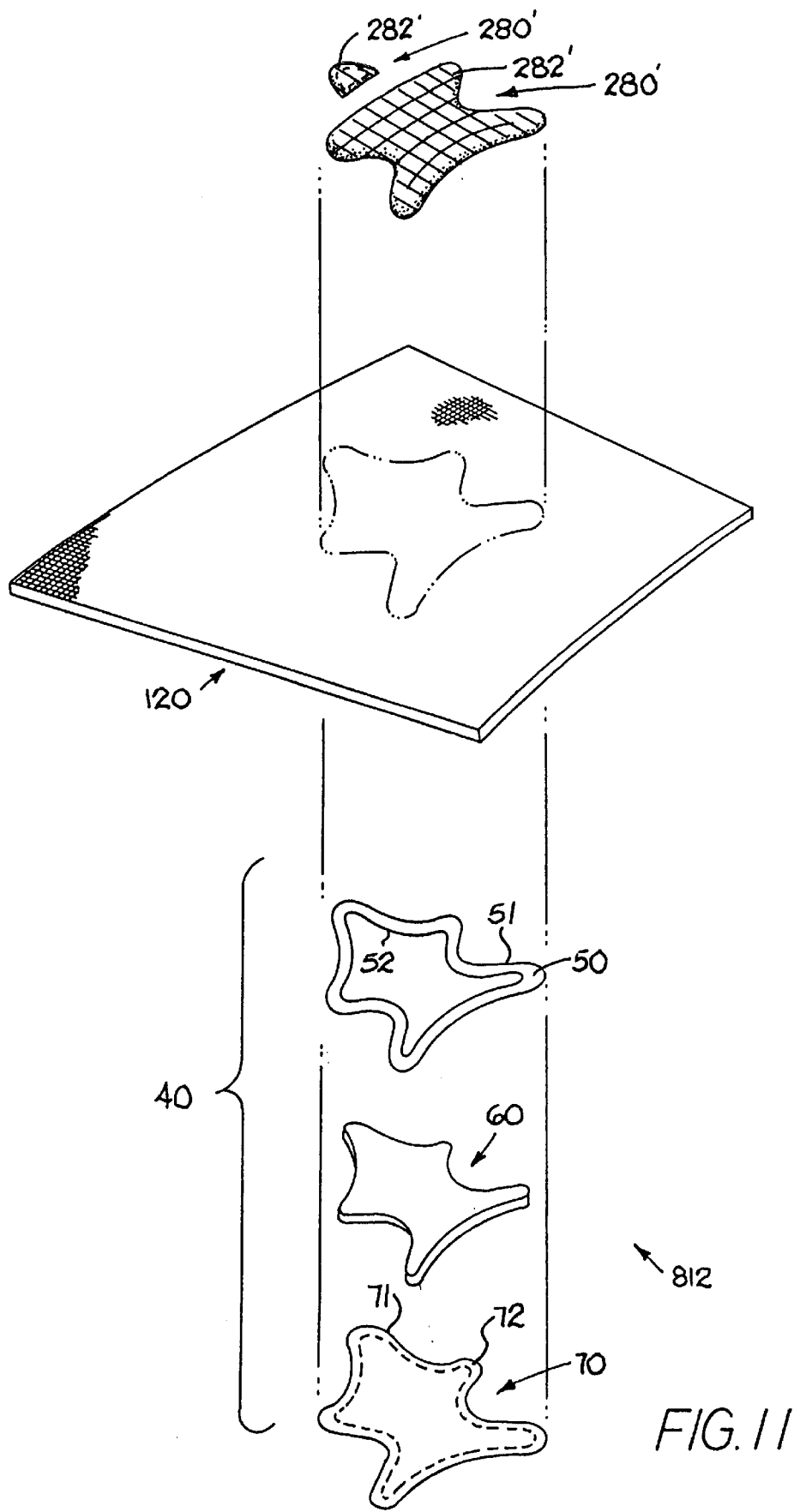
FIG. 11 is the same view as FIG. 3B, but showing a sixth alternative embodiment of the protective attachment.

FIG. 11 shows an alternative embodiment of a brace 812, including a shell 280 made up of two flat plastic pieces, 280, 280', made of a rigid or semi-rigid meltable material, such as polyvinyl chloride, PETG, amorphous polyethylene terephthalate (APET), or any combination thereof. The flat plastic pieces 280, 280' having allowances 282, 282', are cut to complement the shape and size of the protective attachment 40, but they can cover less than the entire surface of the attachment 40. To join the shell pieces 280, 280' to the base 120 of the knee brace 812, an RF-sealed seam is made across the allowances 282, 282' of the flat shell pieces 280, 280'. The flat shell pieces 280, 280' can also be covered with an external covering, in the same manner as described for the brace of FIG. 10B.

EXAMPLE 11

Referring to FIG. 11, the shell pieces 280, 280', made of PVC with a thickness of about 0.040", and having allowances 282, 282' of about 0.5", are attached with an RF-sealed seam to the base 120 of Example 4, using a power setting of about 29.5%, pre-seal time of about 2 seconds, seal time of about 6 seconds, dwell time of about 7 seconds, pressure of about 80 PSI, and the heated platen at about 200° F. The protective attachment 40 is then assembled and attached to the opposite face of base 120 as in Example 4.

Figure 12:
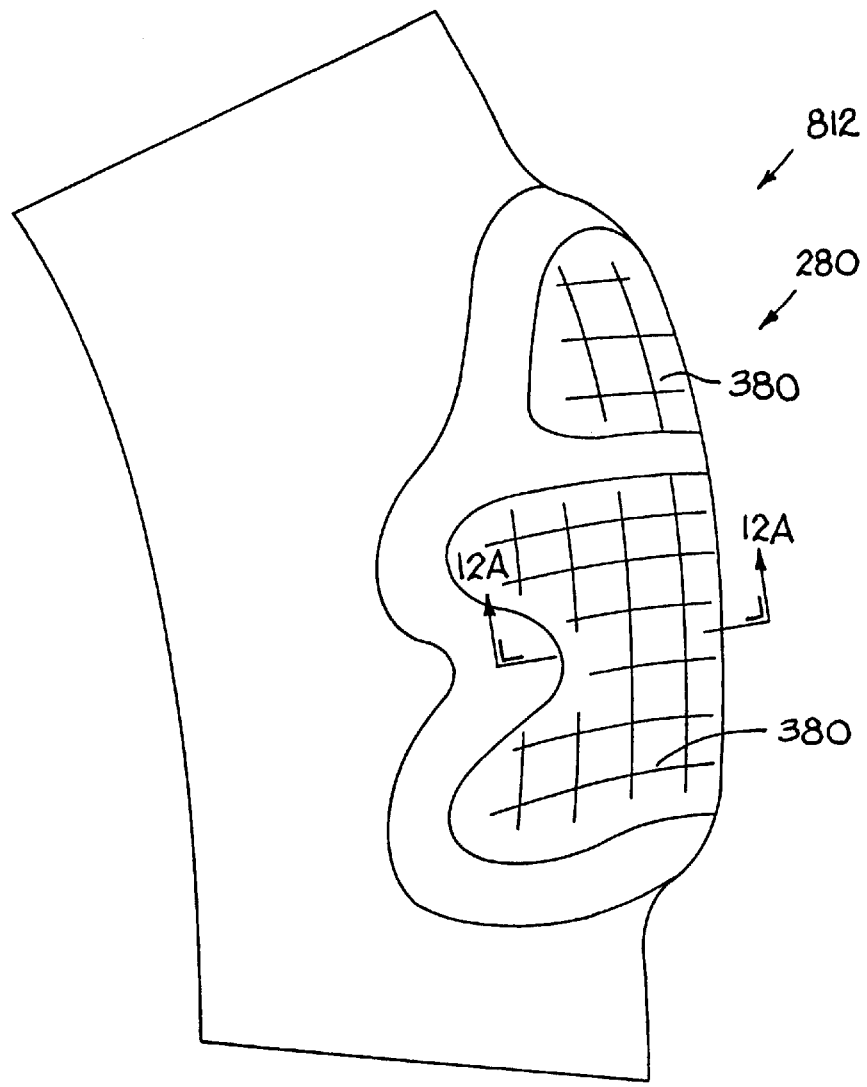
FIG. 12 is a perspective view of the assembled knee brace of FIG. 11.
Figure 12A:
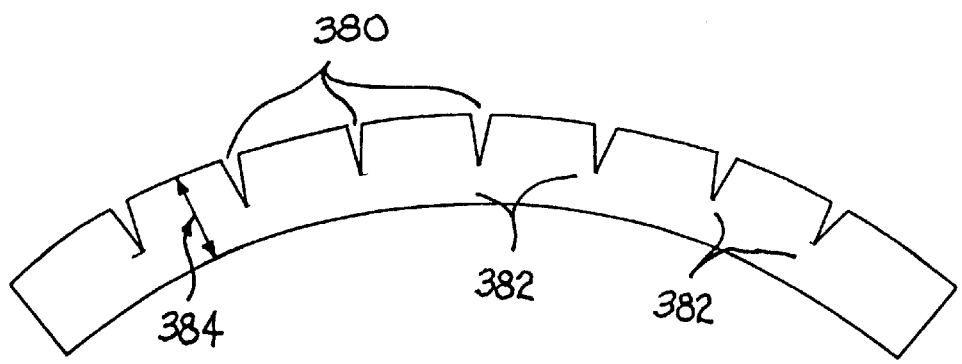
FIG. 12A is a view taken along the line 12A—12A of FIG. 12.

FIGS. 12 and 12A show how the rigid shell pieces 280, 280' can be scored along lines 380 to produce hinges 382, or flexion points within the material, that will bend and flex with the body. The scoring lines 380 are less than half or approximately half of the thickness 384 of the semi-rigid material. When the shell pieces 280, 280' are scored in the manner described, the shell will flex outwardly, allowing the wearer to bend his knee, but it will be prevented from flexing inwardly, thereby protecting the knee against impact. The formed shells 180, 180' of previous embodiments, can be scored in a similar manner, if desired.

Figure 13:
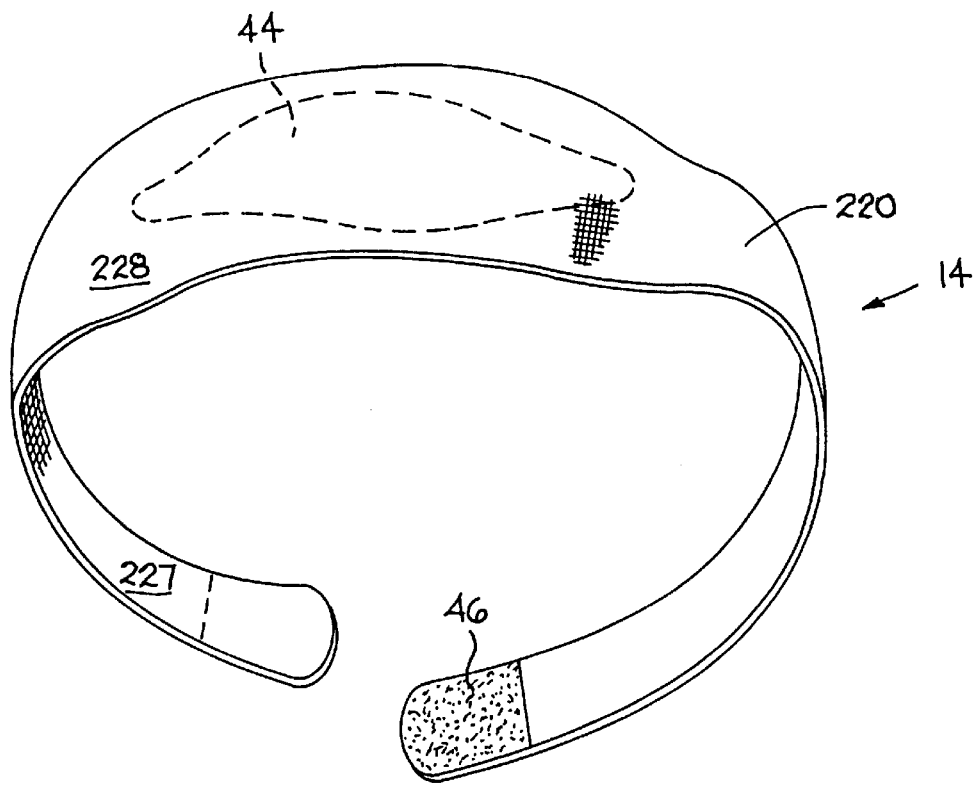
FIG. 13 is a perspective view of the back brace of FIG. 1.

FIG. 13 shows a back brace 14, made in accordance with the present invention. In this case, the base material 220 is made from a foamed polymer sheet 228, similar to the polymer sheet 128 of FIG. 3, and is laminated to a single layer fabric-like material 227, having interstices, similar to the single layer material 127 of FIG. 3. The base 220 is cut into a shape suitable to fit around a person's waist, to and a Velcro fastener 46 is used. The protective attachment 44, made of the same materials and attached in the same way as protective attachment 40 of FIG. 2, is shaped to provide support to the back, and is secured to the base material 220 on the side of the fabric-like material 227, making an RF-sealed seam, as described with respect to previous embodiments.

Figure 14:
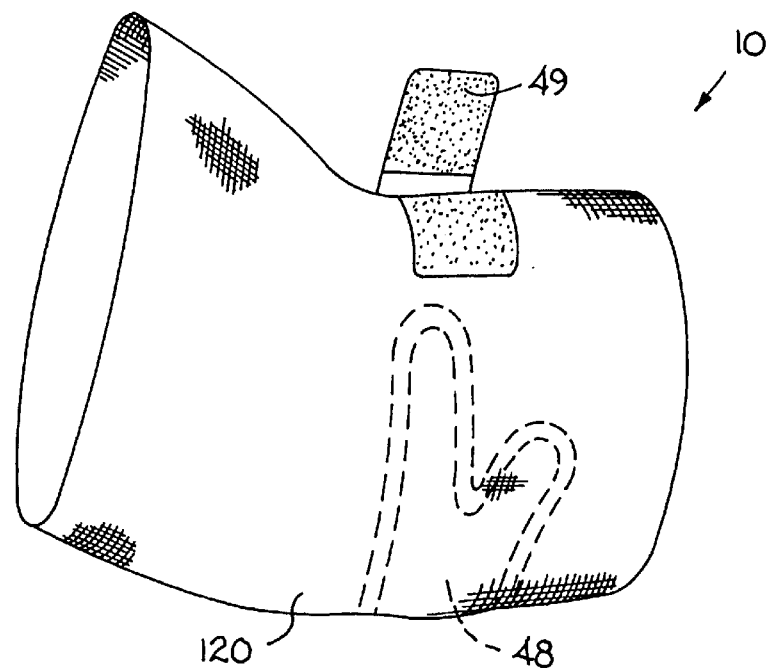
FIG. 14 is a perspective view of the elbow brace of FIG. 1.

FIG. 14 shows an elbow brace 10, also made in accordance with the present invention. The base 120 of flexible material is sized to fit over an arm rather than a leg, and the protective attachment 48, made of the same materials and attached in the same way as protective attachment 40 of FIG. 2, is secured onto the base 120. A strap 49 is added to permit the wearer to tighten the brace 10 onto the arm. Straps may be added to any of the braces if the elasticity of the base material 120 is not sufficient to securely hold the brace in place or if it is desired to increase the pressure of the brace at certain points.

It will be obvious to those skilled in the art that modifications may be made to the embodiments described above without departing from the scope of the present invention.

What is claimed is:

1. An athletic brace, comprising:
   a base material;
   a cover material, having a periphery and an allowance;
   at least one layer of thermoplastic material, between the cover material allowance and the base, said thermoplastic material securing said base material to said cover material along said allowance, to form a seam, thereby defining a niche space between said cover and said base; and
   a first cushioning component, encased in said niche space.

2. The athletic brace as recited in claim 1, wherein said first cushioning component extends into the seam, and said cover material, thermoplastic material, cushioning component, and base material are attached together at said seam.

3. The athletic brace as recited in claim 2, wherein said first cushioning component has a dielectric dissipation factor greater than about 0.04.

4. The athletic brace as recited in claim 3, wherein said first cushioning component is selected from the group consisting of ethyl vinyl acetate copolymer foam, polyurethane foam, polyvinyl chloride foam, and combinations thereof.

5. The athletic brace as recited in claim 1, wherein said first cushioning component terminates short of said seam.

6. The athletic brace as recited in claim 5, wherein said first cushioning component is selected from the group consisting of gas-filled envelopes, gel-filled envelopes, fluid-filled envelopes, meltable foam, semi-rigid impact resistant material, rigid impact resistant material, and combinations thereof.

7. The athletic brace as recited in claim 6, wherein said first cushioning component is selected from the group consisting of ethyl vinyl acetate copolymer foam, polyurethane foam, polyvinyl chloride foam, low density polyethylene foam, vinyl nitrile foam, polyvinyl chloride foam, and combinations thereof.

8. The athletic brace as recited in claim 1, wherein the first cushioning component defines a void space, and further comprising a second cushioning component located in the void space.

9. The athletic brace as recited in claim 8, wherein said first cushioning component has a dielectric dissipation factor greater than about 0.04, so said first cushioning component can be activated by a radio frequency energy source, and wherein said second cushioning component is selected from the group consisting of gas-filled envelopes, gel-filled envelopes, fluid-filled envelopes, foam, semi-rigid impact resistant material, rigid impact resistant material, and combinations thereof.

10. The athletic brace as recited in claim 1, wherein said thermoplastic material has a dielectric dissipation factor greater than about 0.04.

11. The athletic brace as recited in claim 10, wherein said thermoplastic material is selected from the group consisting of ethyl vinyl acetate copolymer, polyurethane, polyvinyl chloride, and combinations thereof.

12. The athletic brace as recited in claim 1, wherein said first cushioning component is selected from the group consisting of foam, semi-rigid impact resistant material, rigid impact resistant material, gas-filled envelopes, gel-filled envelopes, fluid-filled envelopes, gas, gel, fluid, and combinations thereof.

13. The athletic brace as recited in claim 1, wherein said base material is a first sheet of stretchable material having interstices.

14. The athletic brace as recited in claim 13, wherein said first sheet of stretchable material is a woven, non-woven, or knitted fabric.

15. The athletic brace as recited in claim 1, wherein said base material is a first sheet of stretchable material, having interstices, laminated to a layer of foam.

16. The athletic brace as recited in claim 15, wherein the layer of foam is a foamed polymer.

17. The athletic brace as recited in claim 16, wherein the layer of foam is selected from the group consisting of foamed polyethylene, foamed polypropylene, foamed polyisoprene, neoprene, cross-linked polyolefin, and combinations thereof.

18. The athletic brace as recited in claim 15, wherein said first sheet of stretchable material is nylon and said layer of foam is neoprene.

19. The athletic brace as recited in claim 1, wherein said base material is a layered structure comprising first and second sheets of stretchable material having interstices; and a layer of foam between said first and second sheets of stretchable material.

20. The athletic brace as recited in claim 19, wherein said first and second sheets of stretchable material are made of the same material.

21. The athletic brace as recited in claim 19, wherein said first and second sheets of stretchable material are made of different materials.

22. The athletic brace as recited in claim 19, wherein said first and second sheets of stretchable material are nylon and said foam is neoprene.

23. The athletic brace as recited in claim 1, wherein said cover material is a first sheet of stretchable material having interstices.

24. The athletic brace as recited in claim 23, wherein said first sheet of stretchable material is a woven, non-woven, or knitted fabric.

25. The athletic brace as recited in claim 1, wherein said cover material is a first sheet of stretchable material, having interstices, laminated to a layer of foam.

26. The athletic brace as recited in claim 25, wherein the layer of foam is a foamed polymer.

27. The athletic brace as recited in claim 26, wherein the layer of foam is selected from the group consisting of foamed polyethylene, foamed polypropylene, foamed polyisoprene, neoprene, cross-linked polyolefin, and combinations thereof.

28. The athletic brace as recited in claim 25, wherein said first sheet of material is nylon and said layer of foam is neoprene.

29. The athletic brace as recited in claim 1, wherein said cover material is a layered structure, comprising first and second sheets of stretchable material defining interstices; and a layer of foam between said first and second sheets of stretchable material.

30. The athletic brace as recited in claim 29, wherein said first and second sheets of stretchable material are made of the same material.

31. The athletic brace as recited in claim 29, wherein said first and second sheets of stretchable material are made of different materials.

32. The athletic brace as recited in claim 29, wherein said first and second sheets of stretchable material are nylon and said foam is neoprene.

33. The athletic brace as recited in claim 1, wherein said cover material is a thermoplastic polymer having a dielectric dissipation factor greater than about 0.04, so said cover material can be activated by a radio frequency energy source.

34. The athletic brace as recited in claim 33, wherein said cover material is selected from the group consisting of polyvinyl chloride film, urethane film, urethane coated nylon film, polyvinyl chloride coated nylon film, ethyl vinyl acetate coated nylon film, or combinations thereof.

35. The athletic brace as recited in claim 33, wherein said cover and said layer of thermoplastic material form a bladder, and said cushioning component is selected from the group consisting of gas, gel, fluid, and foam, and is located inside said bladder.

36. An athletic brace, comprising:
  a base material, having interstices; and
  a plastic cover sheet, having a periphery and an allowance, said plastic cover sheet having a dielectric dissipation factor greater than about 0.04, having a thickness greater than 10 mils, and having a Rockwell Hardness "R"-scale value greater than 50, said plastic sheet being secured to said base material along the allowance by melting the plastic cover sheet, thereby forming a seam and defining a niche space between said base material and said plastic cover sheet inside said seam.

37. The athletic brace as recited in claim 36, wherein the plastic cover sheet is a flat sheet.

38. The athletic brace as recited in claim 36, wherein the plastic cover sheet is molded into a predetermined shape.

39. The athletic brace as recited in claim 36, further comprising a cushioning material located in said niche space and extending into the seam.

40. The athletic brace as recited in claim 39, wherein said cushioning material has a dielectric dissipation factor greater than about 0.04, so said cushioning material can be activated by a radio frequency energy source.

41. The athletic brace as recited in claim 40, wherein said cushioning material is selected from the group consisting of meltable foam, semi-rigid impact resistant material, rigid impact resistant material, gas-filled envelopes, gel-filled envelopes, fluid-filled envelopes, and combinations thereof.

42. The athletic brace as recited in claim 36, further comprising a cushioning material located in said niche space and terminating short of said seam.

43. The athletic brace as recited in claim 42, wherein said cushioning material is selected from the group consisting of gas-filled envelopes, gel-filled envelopes, fluid-filled envelopes, foam, semi-rigid impact resistant material, rigid impact resistant material, and combinations thereof.

44. The athletic brace as recited in claim 36, wherein said plastic sheet is selected from the group consisting of polyvinyl chloride, polyethylene terephthalate, amorphous polyethylene terephthalate, high density polyethylene—ethyl vinyl acetate copolymer, PETG, and combinations thereof.

45. The athletic brace as recited in claim 36, wherein said base material comprises a first sheet of stretchable fabric.

46. The athletic brace as recited in claim 36, wherein said base material is a first sheet of stretchable material, having interstices, laminated to a layer of foam.

47. The athletic brace as recited in claim 46, wherein the layer of foam is a foamed polymer.

48. The athletic brace as recited in claim 46, wherein said first sheet of stretchable material is nylon and said layer of foam is neoprene.

49. The athletic brace as recited in claim 36, wherein said base material is a layered structure, comprising first and second sheets of stretchable material having interstices; and a layer of foam between said first and second sheets of stretchable material.

50. The athletic brace as recited in claim 49, wherein said first and second sheets of stretchable material are the same.

51. The athletic brace as recited in claim 49, wherein said first and second sheets of stretchable material are different.

52. The athletic brace as recited in claim 49, wherein said first and second sheets of stretchable material are nylon and said foam is neoprene.

53. An athletic brace, comprising:
  a base material, having interstices; and
  a plastic cover sheet, having a periphery and an allowance, said plastic cover sheet having a dielectric dissipation factor greater than about 0.04, and having a thickness greater than 10 mils, said plastic cover sheet being secured to said base material along the allowance by melting the plastic cover sheet, thereby forming a seam and defining a niche space between said base material and said plastic cover sheet inside said seam; and
  a first cushioning component, encased in said niche space, and terminating short of said plastic cover sheet allowance.

54. The athletic brace as recited in claim 53, wherein said plastic cover sheet is selected from the group consisting of polyvinyl chloride, polyethylene terephthalate, amorphous polyethylene terephthalate, high density polyethylene—ethyl vinyl acetate copolymer, PETG, and combinations thereof.

55. The athletic brace as recited in claim 53, wherein said cushioning material is selected from the group consisting of gas-filled envelopes, gel-filled envelopes, fluid-filled envelopes, foam, gel, fluid, semi-rigid impact resistant material, rigid impact resistant material, and combinations thereof.

56. The athletic brace as recited in claim 53, wherein said base material comprises a first sheet of stretchable fabric.

57. The athletic brace as recited in claim 53, wherein said base material is a layered structure, comprising first and second sheets of stretchable material having interstices; and a layer of foam between said first and second sheets of stretchable material.

58. The athletic brace as recited in claim 57, wherein said first and second sheets of stretchable material are nylon and said foam is neoprene.

* * * * *

UNITED STATES PATENT AND TRADEMARK OFFICE
CERTIFICATE OF CORRECTION

PATENT NO : 6,129,695
DATED : October 10, 2000
INVENTOR(S) : Rick Peters, Dolph Smith, and Adam Smith It is certified that error appears in the above-identified patent and that said Letters Patent is hereby corrected as shown below:

Column 13, line 7, after "person's waist," delete "to".

Signed and Sealed this

Eighth Day of May, 2001

Attest:

NICHOLAS P. GODICI

*Attesting Officer*     *Acting Director of the United States Patent and Trademark Office*